(12) United States Patent
Shannon et al.

(10) Patent No.: US 8,471,014 B2
(45) Date of Patent: Jun. 25, 2013

(54) PROCESS OF MAKING GYRASE AND TOPOISOMERASE IV INHIBITORS

(75) Inventors: Dean Shannon, Milford, MA (US); Tiansheng Wang, Concord, MA (US); Simon Giroux, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/349,884

(22) Filed: Jan. 13, 2012

(65) Prior Publication Data

US 2012/0184742 A1    Jul. 19, 2012

Related U.S. Application Data

(60) Provisional application No. 61/432,990, filed on Jan. 14, 2011.

(51) Int. Cl.
| | | |
|---|---|---|
| C07D 401/00 | (2006.01) | |
| C07D 403/00 | (2006.01) | |
| C07D 405/00 | (2006.01) | |
| C07D 409/00 | (2006.01) | |
| C07D 411/00 | (2006.01) | |
| C07C 413/00 | (2006.01) | |

(52) U.S. Cl.
USPC ........................................................ 544/333

(58) Field of Classification Search
USPC ........................................................ 544/333
See application file for complete search history.

(56) References Cited

U.S. PATENT DOCUMENTS

| | | |
|---|---|---|
| 3,856,957 A | 12/1974 | Seng et al. |
| 4,174,400 A | 11/1979 | Mrozik |
| 4,512,998 A | 4/1985 | Nafissi-Varchei |
| 5,529,998 A | 6/1996 | Habich et al. |
| 5,643,935 A | 7/1997 | Dykstra et al. |
| 6,632,809 B2 | 10/2003 | Grillot et al. |
| RE40,245 E | 4/2008 | Grillot et al. |
| 7,414,046 B2 * | 8/2008 | Grillot et al. ............... 514/215 |
| 7,495,014 B2 | 2/2009 | Charifson et al. |
| 7,569,591 B2 | 8/2009 | Charifson et al. |
| 7,582,641 B2 | 9/2009 | Charifson et al. |
| 7,618,974 B2 | 11/2009 | Charifson et al. |
| 7,674,801 B2 | 3/2010 | Basarab et al. |
| 7,727,992 B2 | 6/2010 | Charifson et al. |
| 7,977,340 B2 | 7/2011 | Haydon et al. |
| 8,034,832 B2 | 10/2011 | Charifson et al. |
| 8,067,606 B2 | 11/2011 | Charifson et al. |
| 8,188,095 B2 | 5/2012 | Charifson et al. |
| 8,193,352 B2 | 6/2012 | Charifson et al. |
| 2004/0043989 A1 | 3/2004 | Grillot et al. |
| 2004/0235886 A1 | 11/2004 | Charifson et al. |
| 2005/0038247 A1 | 2/2005 | Charifson et al. |
| 2005/0256136 A1 | 11/2005 | Charifson et al. |
| 2006/0025424 A1 | 2/2006 | Charifson et al. |
| 2006/0122196 A9 | 6/2006 | Charifson et al. |
| 2008/0132546 A1 | 6/2008 | Basarab et al. |
| 2009/0176771 A1 | 7/2009 | Charifson et al. |
| 2009/0197877 A1 | 8/2009 | Haydon et al. |

(Continued)

FOREIGN PATENT DOCUMENTS

| | | |
|---|---|---|
| EP | 0433648 | 6/1991 |
| EP | 0738726 | 10/1996 |

(Continued)

OTHER PUBLICATIONS

Beers, M. H., and Berkow, R., "The Merck Manual of Diagnosis and Therapy", 7th Edition, Chapter 156—Bacteremia and Septic Shock, Merck Research Laboratories, Whitehouse Station, NJ pp. 1143-1147 (1999).
Champoux, J.J., Annu. Rev. Biochem., 2001, 70, pp. 369-413.
Charifson et al., J. Med. Chem., 2008, 51, pp. 5243-5263.
Charles W. Stratton, MD. "In Vitro Susceptibility Testing Versus in Vivo-Effectiveness" The Medical Clinics of North America 2006, 90, 1077-1088.
Drlica and Zhao, Microbiology and Molecular Biology Reviews, 1997, 61, pp. 377-392.
Joseph E. Drumm et al., "Facile preparation of fused ring azolylureas," 48 Tetrahedron Lett. 5535-5538 (2007).
Stephen P. East et al., "DNA gyrase (GyrB)/topoisomerase IV (ParE) inhibitors," 19 Bioorg. Med. Chem. Lett. 894-899 (2009).

(Continued)

*Primary Examiner* — James O Wilson
*Assistant Examiner* — Alexander R Pagano
(74) *Attorney, Agent, or Firm* — Brinks Hofer Gilson & Lione; William R. Boudreaux; Bashir M. Ali

(57) ABSTRACT

The present application is directed to compounds, intermediates and methods for preparing compounds of formula (I)

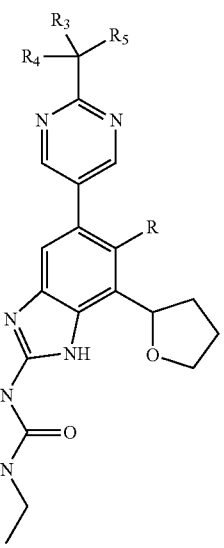

(I)

or a pharmaceutically acceptable salts thereof, wherein R is H or F, and each of $R_3$, $R_4$, and $R_5$ are as defined herein. The compounds of formula (I) and pharmaceutical compositions comprising said compounds and salts inhibit bacterial gyrase and/or Topo IV and are useful in treating bacterial infections.

24 Claims, 2 Drawing Sheets

U.S. PATENT DOCUMENTS

| | | | |
|---|---|---|---|
| 2009/0325935 | A1 | 12/2009 | Charifson et al. |
| 2010/0063069 | A1 | 3/2010 | Charifson et al. |
| 2010/0311766 | A1 | 12/2010 | Haydon et al. |
| 2011/0104207 | A1 | 5/2011 | Charifson et al. |
| 2011/0166088 | A1 | 7/2011 | Sattigeri et al. |
| 2011/0263590 | A1 | 10/2011 | Haydon et al. |
| 2012/0004221 | A1 | 1/2012 | Haydon et al. |
| 2012/0010222 | A1 | 1/2012 | Charifson et al. |
| 2012/0184512 | A1* | 7/2012 | Le Tiran et al. ............... 514/86 |
| 2012/0184564 | A1* | 7/2012 | Shannon et al. ............ 514/256 |
| 2012/0184741 | A1* | 7/2012 | Shannon et al. ............ 544/333 |
| 2012/0184742 | A1 | 7/2012 | Shannon et al. |

FOREIGN PATENT DOCUMENTS

| | | |
|---|---|---|
| EP | 1055668 | 11/2000 |
| WO | WO 99/35155 | 7/1999 |
| WO | WO 00/49015 | 8/2000 |
| WO | WO 00/71522 | 11/2000 |
| WO | WO 02/060879 | 8/2002 |
| WO | WO 03/105846 | 12/2003 |
| WO | WO 2005/012292 | 10/2005 |
| WO | WO 2006/022773 | 3/2006 |
| WO | WO 2007/056330 | 5/2007 |
| WO | WO 2007/148093 | 12/2007 |
| WO | WO 2008/068470 | 6/2008 |
| WO | WO 2009/074810 | 6/2009 |
| WO | WO 2009/074812 | 6/2009 |
| WO | WO 2009/156966 | 12/2009 |
| WO | WO 2011/032050 | 3/2011 |
| WO | WO 2011/047323 | 4/2011 |
| WO | WO 2012/045124 | 4/2012 |

OTHER PUBLICATIONS

Eckert et al., "The antifungal activity of . . . " CA 93:39290 (1980).
Gershman in The Medical Reporter, 1997.
Guven et al. "Synthesis and Antimicrobial Activity of Some Novel Furyl and Benzimidazole Substituted Benzyl Ethers" Journal of Heterocyclic Chemistry 2007, 44, 731.
He et al. "Synthesis and biological evaluation of novel benzimidazoles as potential antibacterial agents." Bioorganic & Medicinal Chemistry Letters 2004, 14, 1217-1220.
Hubschwerlen et al., "Pyrimido[1,6-1]benzimidazoles: A New Class of DNA Gyrase Inhibitors" J. Med. Chem, vol. 35, No. 8, pp. 1385-1392, 1992.
International Search Report and Written Opinion of the International Searching Authority, International Patent Application No. PCT/US2012/021270 (Mar. 16, 2012).
International Search Report and Written Opinion of the International Searching Authority, International Patent Application No. PCT/US2012/021281 (May 3, 2012).
International Search Report and Written Opinion of the International Searching Authority, International Patent Application No. PCT/US2012/021280 (Mar. 23, 2012).
International Search Report and Written Opinion of the International Searching Authority, International Patent Application No. PCT/US2012/021275 (Mar. 23, 2012).
Kornberg and Baker, DNA Replication, 2d Ed., Chapter 12, 1992, W. H. Freeman and Co.
Kus, C., "Synthesis and Antimicrobial Activities of 5-fluoro-1, 2, 6-trisubstituted benzimidazole carboxamide and acetamide derivatives," Arch. Pharm. Pharm. Med. Chem. 334(11):361-365 (2001).
Levy, "The Challenge of Antibiotic Resistance", Scientific American, Mar. 1998).
Lewis, "The Rise of Antibiotic-Resistant Infections", FDA Consumer magazine, Sep. 1995.
Maxwell, Mol. Microbiol., 1993, 9, 681.
Maxwell, Trends in Microbiology, 1997, 5, 102.
MayoClinic "Antibiotic associated diarrhea" Mayoclinic.com. (2007).
Nicolaus B.J.R., "Symbiotic Approach to Drug Design," Decision Making in Drug Research, pp. 173-186 (1983).
Pea et al., PubMed Abstract (Clin Pharmacokinet. 44(10):1009-34) 2005.
Singh, S.K., et al., "Studies in antiparastic agents: Part 13—Synthtesis of 4-aryl-2-substitutedamino-thiazoles as potential anthelmintics," Indian J. Chem., 28B (9):786-789 (1989).
Skopenka, V.V., et al., "Organotin Carbamoyldicyanomethanide, nitrosocarbamoylcyanomethanide, and Carbamoylcyanides," retrieved from STN Database accession No. 101:230674, XP002254350 abstract and Dopovidi Akademii Nauk Ukrains'Koi RSR, Seriya B: Geologichni, Khimichni Ta Biologichni Nauki, 7:44-46 (1984).
Snyder et al., PubMed Abstract (J. Med Liban. 48(4):208-14), Jul.-Aug. 2000.
Sun et al., "Synthesis and Evaluation of Terbenzimidazoles as Topoisomerase I Inhibitors" J. Med. Chem., vol. 38, No. 18, pp. 3638-3644, 1995.
Tanitame et al. "Design, synthesis and structure-activity relationship studies of novel indazole analogues as DNA gyrase inhibitors with Gram-positive antibacterial activity" Bioorganic & Medicinal Chemistry Letters 2004, 14, 2857-2862.
Drlica, Molecular Microbiology, 1992, 6, 425.
Wassenaar "Bacteria; more than pathogens" Am. Ins. Biol. Sci. Internet p. 1-7 (2002).
Webster's Dictionary (1984) p. 933.
WHO Report, "Use of Quinolones in Food Animals and Potential Impact on Human Health", 1998.

* cited by examiner

PROCESS OF MAKING GYRASE AND TOPOISOMERASE IV INHIBITORS

CROSS REFERENCE TO RELATED APPLICATIONS

This application claims the benefit under 35 U.S.C. §119 of U.S. Provisional Patent Application Ser. No. 61/432,990 filed Jan. 14, 2011, the contents of which are incorporated herein by reference.

BACKGROUND OF THE APPLICATION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as Streptococcus pneumoniae (SP), Mycobacterium tuberculosis, and Enterococcus. The appearance of vancomycin resistant enterococcus was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as Staphylococcus aureus, where methicillin resistance is already prevalent (De Clerq, et al., Current Opinion in Anti-infective Investigational Drugs, 1999, 1, 1; Levy, "The Challenge of Antibiotic Resistance", Scientific American, March, 1998).

Another concern is how quickly antibiotic resistance can spread. For example, until the 1960's SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in The Medical Reporter, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", FDA Consumer magazine, September 1995).

As a result of the need to combat drug-resistant bacteria and the increasing failure of the available drugs, there has been a resurgent interest in discovering new antibiotics. One attractive strategy for developing new antibiotics is to inhibit DNA gyrase and/or topoisomerase IV, bacterial enzymes necessary for DNA replication, and therefore, necessary for bacterial cell growth and division. Gyrase and/or topoisomerase IV activity are also associated with events in DNA transcription, repair and recombination.

Gyrase is one of the topoisomerases, a group of enzymes which catalyze the interconversion of topological isomers of DNA (see generally, Kornberg and Baker, DNA Replication, 2d Ed., Chapter 12, 1992, W.H. Freeman and Co.; Drlica, Molecular Microbiology, 1992, 6, 425; Drlica and Zhao, Microbiology and Molecular Biology Reviews, 1997, 61, pp. 377-392). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain which has the ATPase activity, and a carboxy-terminal domain which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase and/or topoisomerase IV would be selective for these enzymes and be relatively inactive against the eukaryotic type II topoisomerases.

Topoisomerase IV primarily resolves linked chromosome dimers at the conclusion of DNA replication.

The widely-used quinolone antibiotics inhibit bacterial DNA gyrase (GyrA) and/or Topoisomerase IV (ParC). Examples of the quinolones include the early compounds such as nalidixic acid and oxolinic acid, as well as the later, more potent fluoroquinolones such as norfloxacin, ciprofloxacin, and trovafloxacin. These compounds bind to GyrA and/or ParC stabilize the cleaved complex, thus inhibiting overall gyrase function, leading to cell death. The fluoroquinolones inhibit the catalytic subunits of gyrase (GyrA) and/or Topoisomerase IV (Par C) (see Drlica and Zhao, Microbiology and Molecular Biology Reviews, 1997, 61, 377-392). However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

The associated subunits responsible for supplying the energy necessary for catalytic turnover/resetting of the enzymes via ATP hydrolysis are GyrB (gyrase) and ParE (topoisomerase IV), respectively (see, Champoux, J. J., Annu. Rev. Biochem., 2001, 70, pp. 369-413). Compounds that target these same ATP binding sites in the GyrB and ParE subunits would be useful for treating various bacterial infections (see, Charifson et al., J. Med. Chem., 2008, 51, pp. 5243-5263).

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, Trends in Microbiology, 1997, 5, 102).

For coumarin-resistant bacteria, the most prevalent point mutation is at a surface arginine residue that binds to the carbonyl of the coumarin ring (Arg136 in *E. coli* GyrB). While enzymes with this mutation show lower supercoiling and ATPase activity, they are also less sensitive to inhibition by coumarin drugs (Maxwell, Mol. Microbiol., 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, Trends in Microbiology, 1997, 5, 102). It would be desirable to have a new, effective GyrB and ParE inhibitor that overcomes these drawbacks and, preferably does not rely on binding to Arg136 for activity. Such an inhibitor would be an attractive antibiotic candidate, without a history of resistance problems that plague other classes of antibiotics.

As bacterial resistance to antibiotics has become an important public health problem, there is a continuing need to develop newer and more potent antibiotics. More particularly, there is a need for antibiotics that represent a new class of compounds not previously used to treat bacterial infection. Compounds that target the ATP binding sites in both the GyrB (gyrase) and ParE (topoisomerase IV) subunits would be useful for treating various bacterial infections. Such compounds would be particularly useful in treating nosocomial infections in hospitals where the formation and transmission of resistant bacteria are becoming increasingly prevalent.

SUMMARY OF THE APPLICATION

In one embodiment, the present invention provides a method for preparing a compound of formula (I)

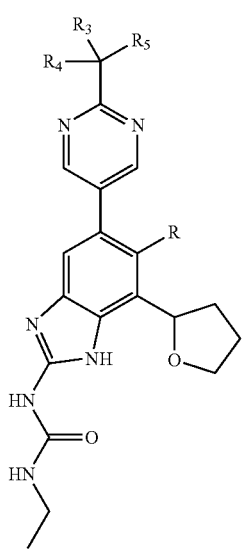

or a pharmaceutically acceptable salt thereof, wherein R is H or F, and each of $R_3$, $R_4$, and $R_5$ is independently an optionally substituted alkyl or an optionally protected hydroxyl group. The method comprises providing a phenylpyrimidine compound of formula (II)

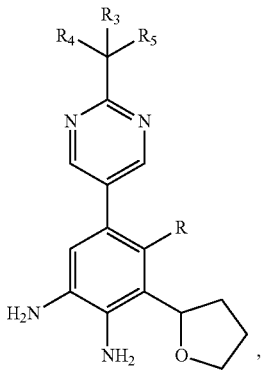

wherein R is H or F, and each of $R_3$, $R_4$, and $R_5$ is independently an optionally substituted alkyl or an optionally protected hydroxyl group;

and reacting the phenylpyrimidine compound of formula (II) with a urea derivative of formula A or B:

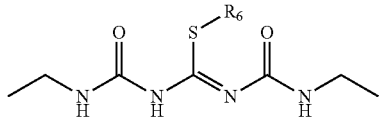

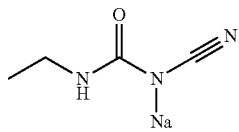

wherein $R_6$ is an optionally substituted alkyl, optionally substituted aryl, optionally substituted saturated or unsaturated carbocycle, or optionally substituted saturated or unsaturated heterocycle, to provide a compound of formula (I); and optionally reacting the compound of formula (I) with a suitable acid to provide a pharmaceutically acceptable salt of the compound of formula (I).

In some aspects of the embodiment, $R_6$ may be methyl, ethyl, benzyl, or p-nitrobenzyl. In a further aspect, the reaction may be conducted in a mixture of dioxane and a buffer at 75° C. to 125° C. In a further aspect, the buffer may be a pH 3.5 buffer and the reaction may be conducted at reflux.

In a second embodiment, the present invention provides a method for preparing a phenylpyrimidine compound of formula (II),

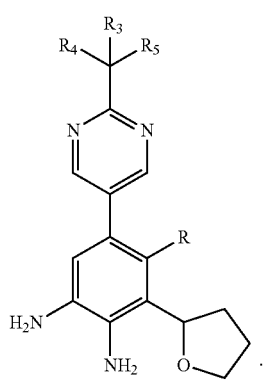 (II)

The method comprises providing a phenyltetrahydrofuran derivative of formula (IV),

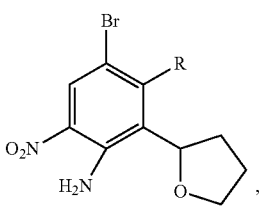 (IV)

wherein R is H or F; and reacting the phenyltetrahydrofuran compound of formula (IV) with a boronic acid derivative of formula (III)

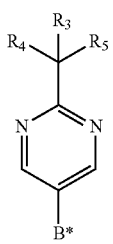 (III)

wherein each of $R_3$, $R_4$, and $R_5$ is independently an optionally substituted alkyl or an optionally protected hydroxyl group, and B* is

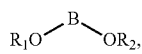

each of $R_1$ and $R_2$ being independently alkyl or H, or $OR_1$ and $OR_2$ together with the B atom to which they are attached forming an optionally substituted 5-, 6-, or 7-membered ring, or $BF_3X$, X being any monovalent cation, in the presence of a palladium catalyst in a polar solvent to provide a phenylpyrimidine compound of formula (V),

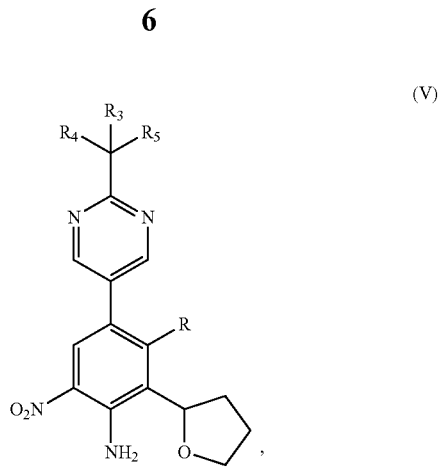 (V)

wherein R is H or F, and each of $R_3$, $R_4$, and $R_5$ is independently an optionally substituted alkyl or an optionally protected hydroxyl group; and treating the phenylpyrimidine compound of formula (V) with a suitable reducing agent to afford the phenylpyrimidine compound of formula (II).

In some aspects of this embodiment, B* may be

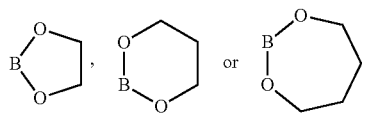

wherein each of the carbon atoms of the ring may be unsubstituted or substituted with one or two methyl or ethyl groups. In a further aspect, B* may be

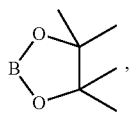

In a third embodiment, the present invention provides a method for preparing a phenyltetrahydrofuran compound of formula (IV),

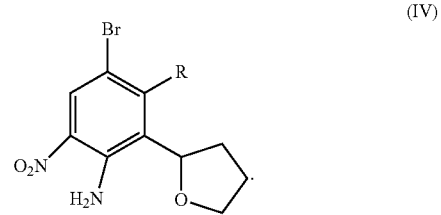 (IV)

The method comprises providing a compound of formula (VI),

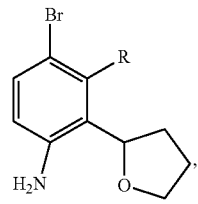
(VI)

wherein R is H or F; and nitrating the compound of formula (VI) with a suitable nitrating agent to afford the phenyltetrahydrofuran compound of formula (IV).

In a fourth embodiment, the present invention provides an alternative method for preparing a phenyltetrahydrofuran compound of formula (IV). The method comprises providing a compound of formula (VI),

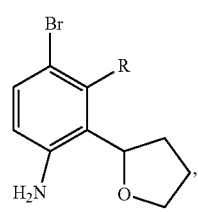
(VI)

wherein R is H or F;
protecting the amino group of the compound of formula (VI) with an amino protecting group to afford an amino-protected compound;
nitrating the amino-protected compound with a suitable nitrating agent to afford an amino-protected nitro compound; and deprotecting the amino-protected nitro compound to afford the phenyltetrahydrofuran compound of formula (IV).

In some aspects of this embodiment, said providing a phenylpyrimidine compound of formula (II) may further comprise reducing a phenylpyrimidine derivative of formula (V),

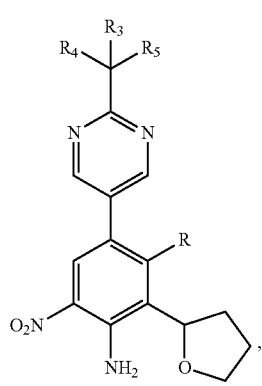
(V)

wherein R is H or F, and each of $R_3$, $R_4$, and $R_5$ is independently an optionally substituted alkyl or an optionally protected hydroxyl group, with a suitable reducing agent to provide the compound of formula (II). In a further aspect, the nitrating the compound of formula (VI) may comprise reacting the compound of formula (VI) with $NH_4NO_3$ in the presence of a strong acid at about 20° C. to about 50° C. to provide a compound (IV).

In a fifth embodiment, the present invention provides a method for preparing a compound of formula (VI),

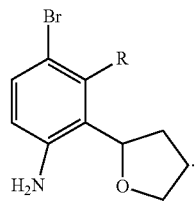
(VI)

The method comprises providing a compound of formula (VII),

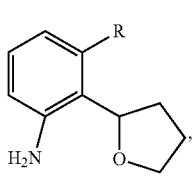
(VII)

wherein R is H or F; and reacting the compound of formula (VII) with a brominating agent in a polar aprotic solvent to afford the compound of formula (VI).

In some aspects of this embodiment, the compound of formula (VII) may be enantiomerically enriched.

In a sixth embodiment, the present invention provides a method for preparing a compound of formula (VII),

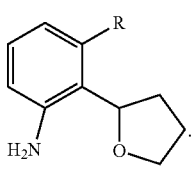
(VII)

The method comprises providing a dihydrofuranyl nitrobenzene compound selected from the group consisting of a compound of formula (VIIIa),

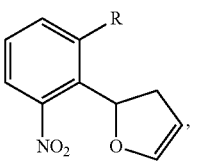
(VIIIa)

wherein R is H or F, and a compound of formula (VIIIb),

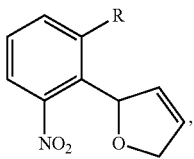

wherein R is H or F; and treating the dihydrofuranyl nitrobenzene compound with a reducing agent to afford the compound of formula (VII).

In a seventh embodiment, the present invention provides a method for preparing a dihydrofuranyl nitrobenzene compound of formula (VIIIa),

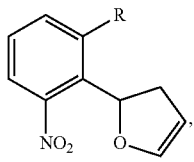

wherein R is H or F, or (VIIIb),

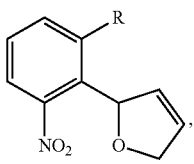

wherein R is H or F, comprising the steps of:
providing a compound of formula (IX),

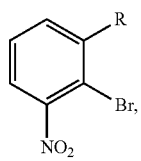

wherein R is H or F; and treating the compound of formula (IX) with 2,3-dihydrofuran in the presence of a palladium catalyst to afford the dihydrofuranyl nitrobenzene compound.

In an eighth embodiment, the present invention provides a compound of the formula

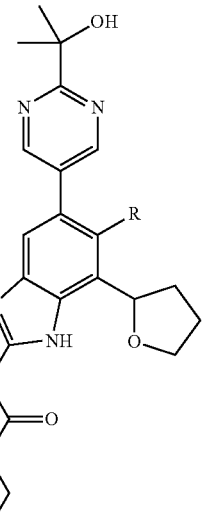

wherein R is H or F, or a pharmaceutically acceptable salt thereof; prepared according to the methods of the present application. In some embodiments, the compound of formula (I) has the formula

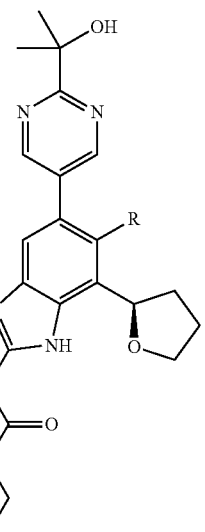

wherein R is H or F, or a pharmaceutically acceptable salt thereof. In other embodiments, the compound of formula (I) may be (R)-1-ethyl-3-(5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof, (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof, a methanesulfonic acid salt of (R)-1-ethyl-3-(5-(2-(2-hydroxypropan-2-yl)pyrimidin-5-yl)-7-(tetrahydrofuran-2-yl)-1H-benzo[d]imidazol-2-yl)urea, or a methanesulfonic acid salt of (R)-1-ethyl-3-(6-fluoro-5-(2-(2- hydroxypropan-2-yl)pyrimidin-5-yl)-7-(tetrahydrofuran-2-yl)-1H-benzo[d]imidazol-2-yl)urea.

In a ninth embodiment, the present application further provides for a compound of formula (II)

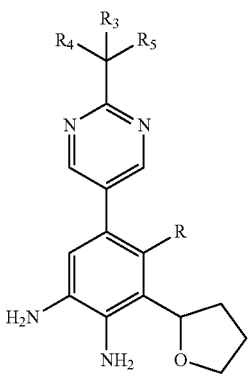

wherein R is H or F, and each of $R_3$, $R_4$, and $R_5$ is independently an optionally substituted alkyl or an optionally protected hydroxyl group. The compound of formula (II) may be prepared by a method comprising providing a phenyltetrahydrofuran derivative of formula (IV)

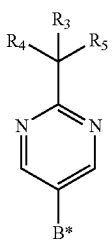

and reacting the phenyltetrahydrofuran derivative of formula (IV) with a boronic acid derivative of formula (III)

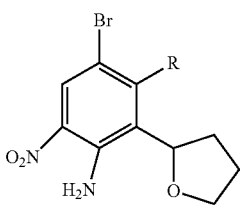

in the presence of a palladium catalyst in a polar solvent; wherein each of $R_3$, $R_4$, and $R_5$ is independently an optionally substituted alkyl or an optionally protected hydroxyl group, and B* is

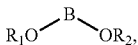

each of $R_1$ and $R_2$ being independently alkyl or H, or $OR_1$ and $OR_2$ together with the B atom to which they are attached forming an optionally substituted 5-, 6-, or 7-membered ring, or $BF_3X$, X being any monovalent cation.

In some aspects of the embodiment, the method further comprises reducing a phenylpyrimidine derivative of formula (V)

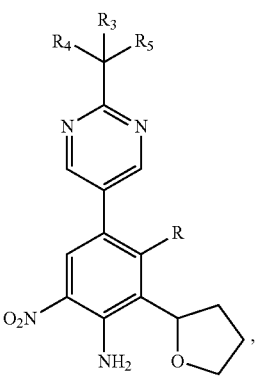

wherein R is H or F, and each of $R_3$, $R_4$, and $R_5$ is independently an optionally substituted alkyl or an optionally protected hydroxyl group, to provide the compound of formula (II).

In a tenth embodiment, the present invention provides a compound of formula (V),

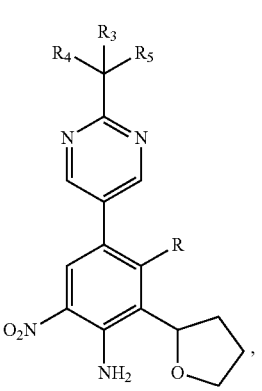

wherein R is H or F; and each of $R_3$, $R_4$, and $R_5$ is independently an optionally substituted alkyl or an optionally protected hydroxyl group. The compound of formula (V) may be prepared by a method comprising providing a phenyltetrahydrofuran derivative of formula (IV)

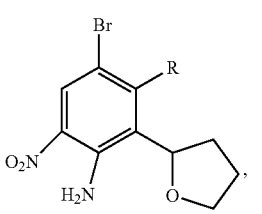

wherein R is H or F, and reacting the phenyltetrahydrofuran derivative of formula (IV) with a boronic acid derivative of formula (III)

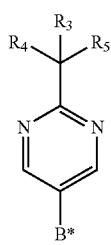
(III)

in the presence of a palladium catalyst in a polar solvent, wherein each of $R_3$, $R_4$, and $R_5$ is independently an optionally substituted alkyl or an optionally protected hydroxyl group, and B* is

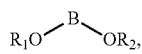

each of $R_1$ and $R_2$ being independently alkyl or H, or $OR_1$ and $OR_2$ together with the B atom to which they are attached forming an optionally substituted 5-, 6-, or 7-membered ring, or $BF_3X$, X being any monovalent cation, to provide the compound of formula (V).

In an eleventh embodiment, the present invention provides a method for preparing a compound of formula (I),

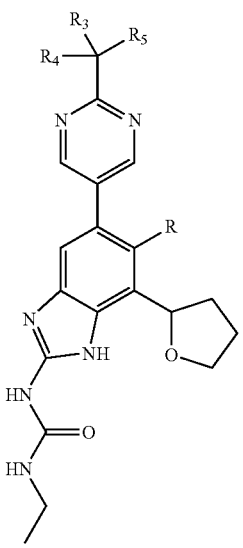
(I)

or a pharmaceutically acceptable salt thereof, wherein R is H or F; and each of $R_3$, $R_4$, and $R_5$ is independently an optionally substituted alkyl or an optionally protected hydroxyl group. The method comprises providing a dihydrofuranyl nitrobenzene compound of formula

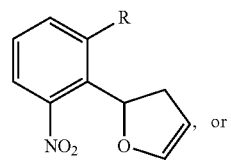
(VIIIa)

or

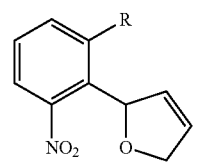
(VIIIb)

wherein R is H or F, and converting the compound of formula (VIIIa) or (VIIIb), or a combination thereof, to the compound of formula (I) or a pharmaceutically acceptable salt thereof.

In a twelfth embodiment, the present invention provides a method for preparing a dihydrofuranyl nitrobenzene compound of formula (VIIIa) or (VIIIb). The method comprises reacting a compound of formula (IX),

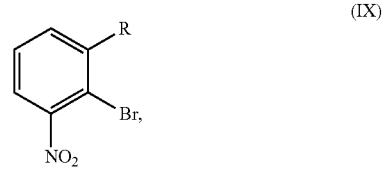
(IX)

wherein R is H or F, with 2,3-dihydrofuran in the presence of a palladium catalyst to afford the dihydrofuranyl nitrobenzene compound (VIIIa) or (VIIIb).

In one aspect of this embodiment, the method further comprises reacting the compound of formula (VIIIa) or (VIIIb) with a reducing agent to afford a compound of formula (VII),

(VII)

wherein R is H or F. In another aspect, the method further comprises reacting the compound of formula (VII) with a brominating agent in a polar aprotic solvent to afford the compound of formula (VI). In a further aspect, the method further comprises nitrating the compound of formula (VI) with a suitable nitrating agent to afford the phenyltetrahydrofuran compound of formula (IV). In yet a further aspect, the method further comprises reacting the phenyltetrahydrofuran compound of formula (IV) with a boronic acid derivative of formula (III)

(III)

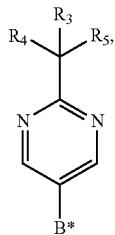

wherein each of $R_3$, $R_4$, and $R_5$ is independently an optionally substituted alkyl or an optionally protected hydroxyl group, and B* is

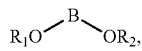

each of $R_1$ and $R_2$ being independently alkyl or H, or $OR_1$ and $OR_2$ together with the B atom to which they are attached forming an optionally substituted 5-, 6-, or 7-membered ring, or $BF_3X$, X being any monovalent cation, in the presence of a palladium catalyst in a polar solvent to provide a phenylpyrimidine compound of formula (V), (V)

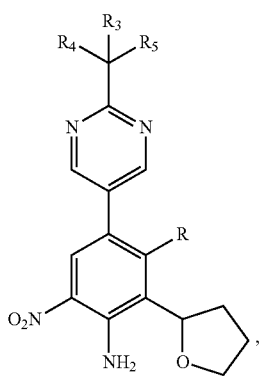

wherein R is H or F, and each of $R_3$, $R_4$, and $R_5$ is independently an optionally substituted alkyl or an optionally protected hydroxyl group; and treating the phenylpyrimidine compound of formula (V) with a suitable reducing agent to afford the phenylpyrimidine compound of formula (II). The method may further comprise reacting the phenylpyrimidine compound of formula (II) with a urea derivative of formula A or B:

A

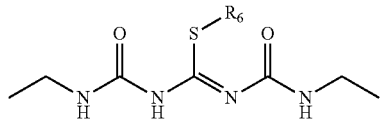

B

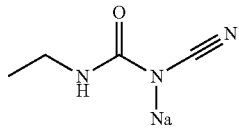

wherein $R_6$ is an optionally substituted alkyl, optionally substituted aryl, optionally substituted saturated or unsaturated carbocycle, or optionally substituted saturated or unsaturated heterocycle; to provide a compound of formula (I); and optionally reacting the compound of formula (I) with a suitable acid to provide a pharmaceutically acceptable salt of the compound of formula (I).

DETAILED DESCRIPTION

Figure 1:
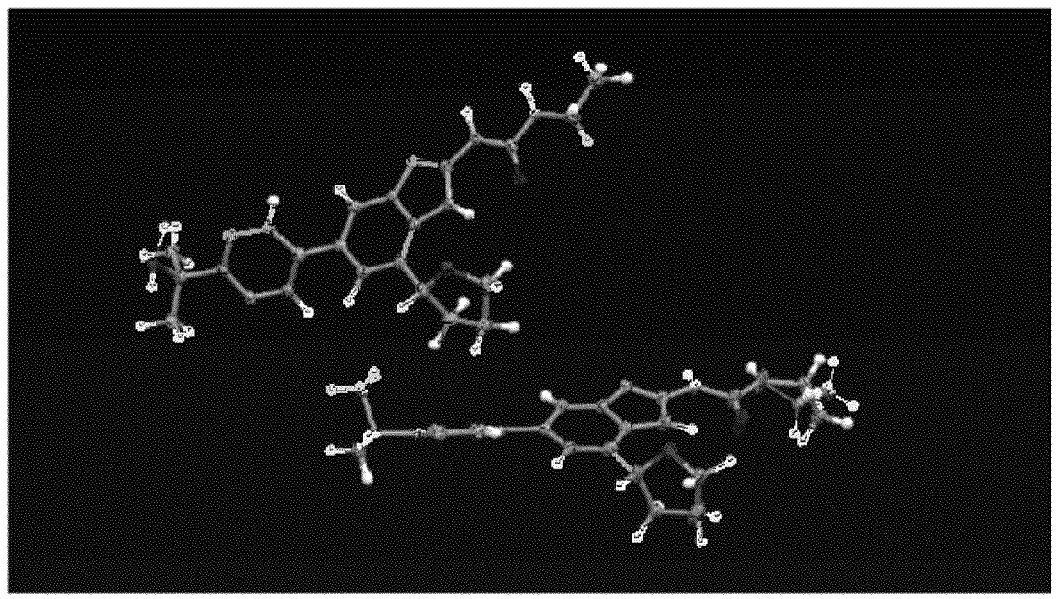
FIG. 1 is a thermal ellipsoid plot of two symmetry independent molecules of compound 12.

The present application is directed to a method of preparing compounds, and pharmaceutically acceptable salts thereof, useful as gyrase inhibitors and antibacterial agents. The gyrase inhibitors of the present application are generically encompassed by U.S. Pat. No. RE40245 E and may be represented by formula (I) or salts thereof:

(I)

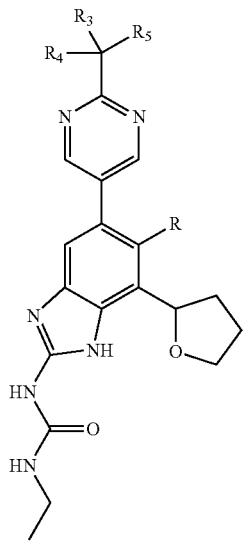

wherein R is H or F; and each of $R_3$, $R_4$, and $R_5$ is independently optionally substituted alkyl or an optionally protected hydroxyl group.

In a particular embodiment, the compounds of the present application may be represented by formula (Ia) or salts thereof:
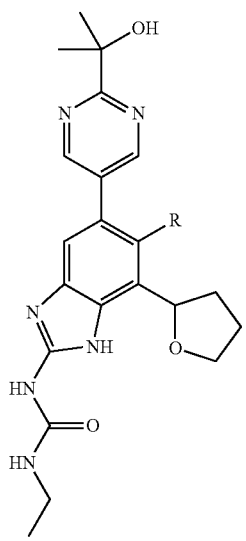
(Ia)
wherein R is H or F.
In certain embodiments, the compound of formula (I) is:
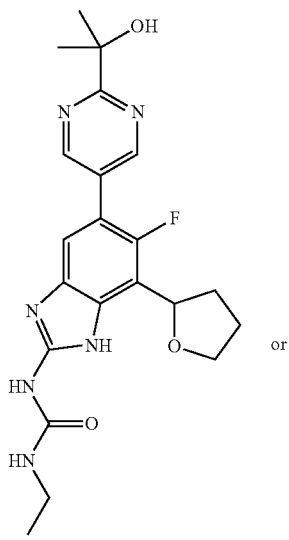
22
or
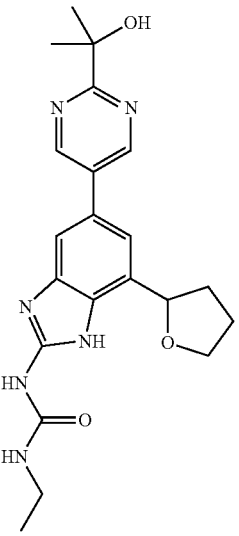
11
In further embodiments, the compound of formula (I) is
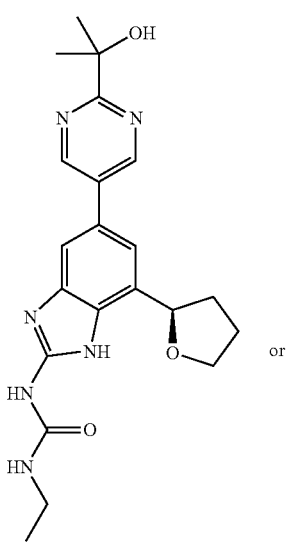
12
or

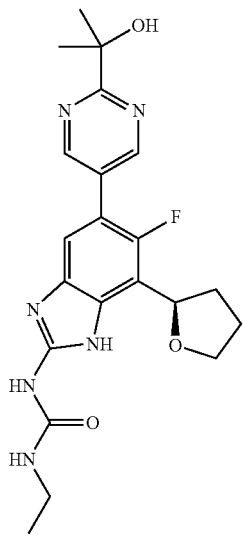
In further embodiments, the compound of formula (I) is
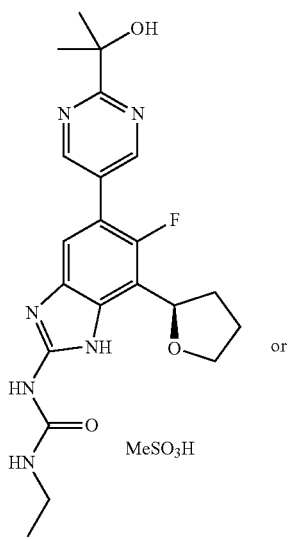 or
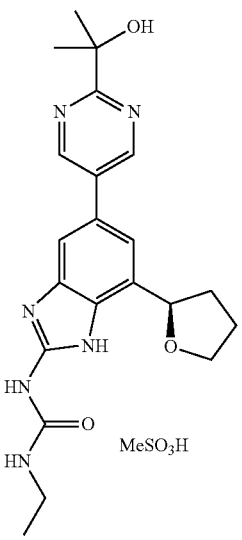
A process for preparing the compound of formula (I) is set forth in Scheme 1.
Scheme 1
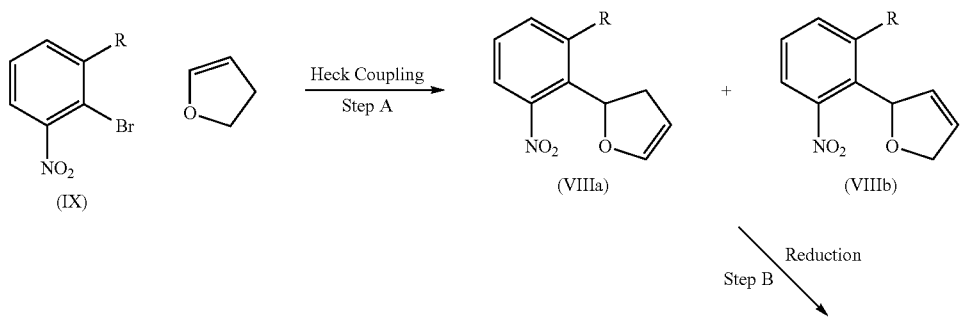

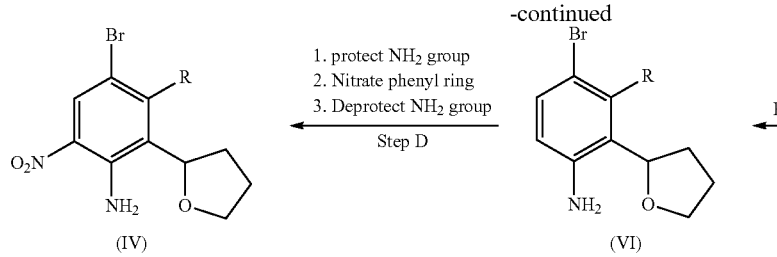
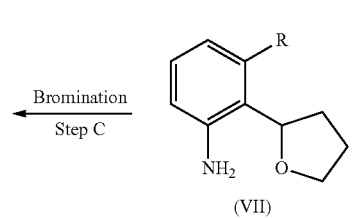
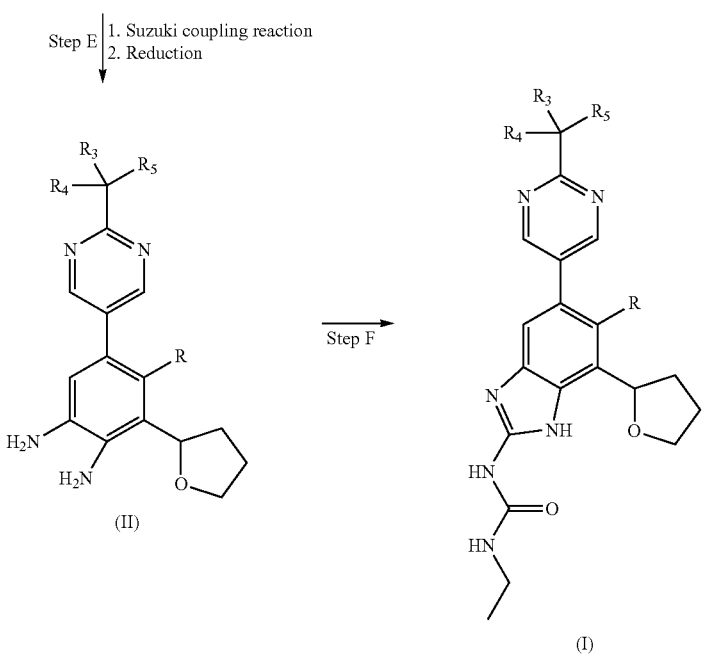

In step A, a bromonitrobenzene (IX), wherein R is H or F, is treated with 2,3-dihydrofuran in the presence of a suitable palladium catalyst and a suitable base. Heck arylation of the 2,3-dihydrofuran affords a mixture of dihydrofuranyl nitrobenzenes (VIIIa) and (VIIIb), wherein R is H or F.

The palladium catalyst used in the Heck arylation reaction may be any suitable palladium catalyst known to those skilled in the art. Examples of palladium catalysts suitable for the Heck arylation reaction between bromonitrobenzene (IX) and 2,3-dihydrofuran include Pd(II), Pd(I), and Pd(0) complexes. In one embodiment, the Pd(II) complex suitable for the present application has the generic formula $PdX_2(phosphine)_2$ wherein X is a monovalent negatively charged group such as a halide group and phosphine as used here refers to the class of compounds in which one, two, or three hydrogen atoms of the compound $PH_3$ is replaced with a corresponding number of groups such phenyl (Ph), cyclohexyl (Cy), tert-butyl (tBu), or isopropyl (iPr). Examples of phosphine ligands suitable for the Pd catalysts of the present application include di-tert-butylmethylphosphine, di-tert-butylneopentylphosphine, dicyclohexyl-(2-methylphenyl)phosphine, dicyclohexyl-(2,4,6-trimethylphenyl)phosphine, tricyclopentylphosphine, tert-butyldiphenylphosphine, cyclohexyldiphenylphosphine, tris(4-chlorophenyl)phosphine, benzyldiphenylphosphine, tri(m-tolyl)phosphine, tris(4-methoxyphenyl)phosphine, 1,3-bis(diphenylphosphino)propane (dppp), 1,2-bis(diphenylphosphino)ethane (dppe), 1,4-bis(diphenylphospino)butane (dppb), meso-2,4-bis (diphenylphosphino)pentane (mbdpp), and 1,3-bis(diisopropylphosphino)propane (dippp). In another embodiment, Pd catalysts suitable for the Heck arylation reaction include $PdCl_2(PPh_3)_2$, $PdCl_2(PCy_3)_2$, $PdCl_2(PiPr_3)_2$, $PdCl_2(PhCN)_2$, $Pd(N,N\text{-dimethyl }\beta\text{-alaninate})_2$, $PdCl_2\{PR_2(Ph\text{-}R')\}_2$ wherein R is tert-butyl and R' is 4-dimethylamino group, bis(dibenzylideneacetone)palladium(II), palladium(II) acetate, $PdCl_2$(bis-hydrazone), [1,3-bis(2,6-diisopropylphenyl)imidazol-2-ylidene](3-chloropyridyl)palladium(II) dichloride, di(2-pyridyl)methanol palladium dichloride, 1,1'-bis(ditert-butylphosphino)ferrocene]dichloropalladium(II), 1,1'-bis(diphenylphosphino)ferrocene]dichloropalladium (II) (Pd(dppf)$Cl_2$), (NHC)Pd(allyl)Cl wherein NHC is an N-heterocyclic carbene such as N,N'-bis(2,6-diisopropylphenyl)imidazol)-2-ylidene, N,N'-bis(2,6-diisopropylphenyl)-4,5-dihydroimidazol)-2-ylidene, N,N'-bis(2,4,6-trimethylphenyl)-imidazole)-2-ylidene, and N,N'-bis tert-butylimidazol)-2-ylidene. In some embodiments, one or more Pd ligands may be tethered to a substrate such as a particle. Examples of such catalysts include $(Ar'Ph_2P)_2PdCl_2$ wherein the Ar' group is part of a polymer such that the catalyst is a polymeric palladium catalyst. In another embodiment, Pd(0) complexes useful in the present application include Pd(phosphine)$_4$ (e.g., Pd(PPh$_3$)$_4$, Pd(PCy$_3$)$_4$, Pd(PiPr$_3$)$_4$, Pd(tBu$_3$P)$_2$, and tris(dibenzylideneacetone)dipalladium(0). In still another embodiment, Pd(I) catalysts useful in the present application include $Pd_2X_2(phosphine)_2$, wherein X is a monovalent anion, such as a halide. Examples of such Pd(I) catalysts include $Pd_2Br_2(tBu_3P)_2$.

In certain embodiments, the palladium catalyst used in the Heck arylation reaction may be any suitable chiral palladium catalyst known to those skilled in the art. Examples of chiral palladium catalysts suitable for the Heck arylation reaction between bromonitrobenzene (IX) and 2,3-dihydrofuran include Pd(II) and Pd(0) complexes of 2,2'-bis(diphenylphosphino)binaphyl (BINAP), other BINAP-type ligands, JosiPhos, other JosiPhos-type ligands, PhanePhos, SynPhos, DifluoroPhos, SegPhos, P-Phos, TunePhos, 2,4-bis(diphenylphosphino)pentane, and PHox. Heck arylation reactions conducted using chiral palladium catalysts may afford enantiomerically-enriched dihydrofuranyl nitrobenzene(s) (VIIIa) and/or (VIIIb), wherein R is H or F. In some embodiments, the enantiomeric excess of dihydrofuranyl nitrobenzene(s) (VIIIa) and/or (VIIIb) may be between about 5-100%, about 10-100%, about 20-100%, about 30-100%, about 40-100%, about 50-100%, about 60-100%, about 70-100%, about 80-100%, about 85-100%, about 90-100%, about 91-100%, about 92-100%, about 93-100%, about 94-100%, about 95-100%, about 96-100%, about 97-100%, about 98-100%, about 99-100%, or about 100%. Thus, any chiral compound derived from the enantiomerically-enriched compound(s) of formula (VIIIa) and/or (VIIIb) may also contain an excess of one of the two enantiomers of the compound.

The base used in the Heck arylation reaction may be any suitable base known to those skilled in the art. Examples of bases suitable for the Heck arylation reaction between bromonitrobenzene (IX) and 2,3-dihydrofuran include potassium carbonate, sodium carbonate, cesium carbonate, sodium bicarbonate, potassium phosphate, sodium tert-butoxide, potassium tert-butoxide, triethylamine, diisopropylethylamine, 1,8-bis(dimethylamino)naphthalene, dicyclohexylamine, dicyclohexylmethlyamine, 2,6-lutidine, sodium acetate, and potassium acetate.

The solvent used for the Heck arylation reaction may be any suitable solvent known to those skilled in the art. Examples of solvents suitable for the Heck arylation reaction between bromonitrobenzene (IX) and 2,3-dihydrofuran include 1,4-dioxane, tetrahydrofuran, 1,2-dimethoxyethane, toluene, N,N-dimethylformamide, dimethylsulfoxide, acetonitrile, and N,N-dimethylacetamide.

The Heck arylation reaction may be conducted at any suitable temperature between 0° C. and 200° C. In some embodiments, the reaction may be conducted between 50 and 150° C. In other embodiments, the reaction may be conducted between 75 and 125° C. In further embodiments, the reaction may be conducted between 90 and 110° C.

In step B, one of dihydrofuranyl nitrobenzenes (VIIIa) and (VIIIb), or a mixture of dihydrofuranyl nitrobenzenes (VIIIa) and (VIIIb), wherein R is H or F, is treated with hydrogen gas in the presence of a transition metal catalyst and a base. Catalytic hydrogenation of the aromatic nitro substituent and the double bond of the dihydrofuranyl substituent affords tetrahydrofuranyl aniline (VII), wherein R is H or F.

The transition metal catalyst used in the catalytic hydrogenation reaction may be any suitable catalyst known to those skilled in the art. Examples of transition metal catalysts suitable for the catalytic hydrogenation of dihydrofuranyl nitrobenzenes (VIIIa) and (VIIIb) include palladium on carbon, platinum on carbon, platinum oxide, etc.

The base used in the catalytic hydrogenation reaction may be any suitable base known to those skilled in the art. Examples of bases suitable for the catalytic hydrogenation of dihydrofuranyl nitrobenzenes (VIIIa) and (VIIIb) include potassium carbonate, sodium carbonate, cesium carbonate, sodium bicarbonate, potassium phosphate, triethylamine, diisopropylethylamine, and other amine bases, such as pyridine, 2,6-lutidine, dicyclohexylmethylamine, pyrrolidine, and methylpyrrolidine.

The catalytic hydrogenation may be conducted in any suitable solvent known to those skilled in the art. Examples of solvents suitable for the catalytic hydrogenation of dihydrofuranyl nitrobenzenes (VIIIa) and (VIIIb) include methanol, ethanol, isopropanol, tetrahydrofuran, 1,4-dioxane, 1,2-dimethoxyethane, ethyl acetate, hexane, and toluene, and any mixtures thereof.

The catalytic hydrogenation reaction may be conducted at any suitable temperature between −50 and 100° C. In some embodiments, the reaction may be conducted between 0 and 50° C. In other embodiments, the reaction may be conducted between 10 and 40° C. In further embodiments, the reaction may be conducted between 20 and 30° C.

The catalytic hydrogenation reaction may be conducted at any suitable pressure of hydrogen gas between 15 psi and 100 psi. In some embodiments, the reaction may be conducted at between 20 and 55 psi. In other embodiments, the reaction may be conducted at between 25 and 50 psi. In further embodiments, the reaction may be conducted at between 30 and 45 psi.

In step C, tetrahydrofuranylaniline (VII), wherein R is H or F, is treated with a suitable brominating agent in a suitable polar aprotic solvent. Bromination of the para position of the tetrahydrofuranylaniline (VII) affords bromoaniline (VI), wherein R is H or F.

The brominating agent used in the bromination reaction may be any suitable brominating agent known to those skilled in the art. Examples of brominating agents suitable for the bromination of tetrahydrofuranylaniline (VII) include N-bromosuccinimide, bromine, and bromamine-T.

The solvent used in the bromination reaction may be any suitable polar aprotic solvent known to those skilled in the art. Examples of solvents suitable for the bromination of tetrahydrofuranylaniline (VII) include acetonitrile, N,N-dimethylformamide, dimethylsulfoxide, hexamethylphosphorictriamide (HMPA), and mixtures of the foregoing solvents with ethereal solvents, such as tetrahydrofuran, diethyl ether, 1,4-dioxane, 1,2-dimethoxyethane, and methyl tert-butyl ether.

The bromination reaction may be conducted at any suitable temperature −78 and 75° C. In one embodiment, the reaction is conducted between −50 and 50° C. In another embodiment, the reaction is conducted between −35 and 35° C. In yet another embodiment, the reaction is conducted between −20 and 10° C.

In step D, the compound of formula (VI) is nitrated to produce the compound of formula (IV). The amino group of the compound of formula (VI), wherein R is H or F, may be protected using any of the variously available protecting groups. Examples of conventional amine protecting groups include alkoxycarbonyl (e.g., tert-butoxycarbonyl known as BOC), 1,1-dioxobenzo[6]thiophene-methoxycarbonyl (Bsmoc), substituted alkoxycarbonyl (such as halogenated alkoxycarbonyl groups such as 2,2,2-trichloroethoxycarbonyl), tert-butyl sulfonyl (BUS), cycloalkoxycarbonyl, bicylicalkoxycarbonyl, alkenyloxycarbonyl, and arylalkoxycarbonyl groups. Examples of these protecting groups are ethoxycarbonyl, cyclopentyloxycarbonyl, cyclohexyloxycarbonyl, 2,2,2-trichloroethoxycarbonyl, allyloxycarbonyl, 1-adamantyloxycarbonyl, t-butyloxycarbonyl, t-amyloxycarbonyl, benzyloxycarbonyl (Cbz), p-nitrobenzyloxycarbonyl, p-methoxybenzyloxycarbonyl, diphenylmethoxycarbonyl. Other nitrogen protecting groups include acyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyrul, benzoyl, 4-chlorobenzoyl, 4-bromobenzoyl, and 4-nitrobenzoyl. Additional amine protection schemes are described in Green, T. W. and Wuts, P. G. M., Protective Groups in Organic Synthesis, John Wiley & Sons, Inc., pp. 494-653 (1999).

The N-protected compound of formula (VI) is nitrated using various nitrating agents known to those skilled in the art. Any reagent that, under appropriate conditions, can introduce a nitro group to the phenyl ring of the compound of formula (VI) may be used. Examples of nitration methods may be found in March, *Advanced Organic Chemistry*, John Wiles & Sons, 2001, pp. 696-699, the contents of which are incorporated herein by reference.

In one embodiment, the nitrating agent may be a mixture of trifluoroacetic anhydride and a nitrate salt. In this embodiment, an excess amount of trifluoroacetic anhydride may be used to protect the amino group of the compound of formula (VI). The protection step is followed by the addition of a nitrate salt to generate a nitrating mixture in situ. For example, ammonium nitrate may be added to generate the active nitrating agent. In some embodiments, the ammonium nitrate may be added in small portions at a temperature of about 30° C., taking care that the temperature remains between 30 and 40° C. Alternatively, an N-protected compound of formula (VI) may be reacted with a mixture of a strong acid and a nitrate salt. For example, a mixture of trifluoroacetic acid and $NH_4NO_3$ may be used to nitrate the N-protected compound of formula (VI).

Other nitrating agents include other inorganic nitrates, organic nitrates, silver nitrate/triphenylphosphine oxide/bromine, lanthanide nosylates, N-nitro-pyridinium and quinolinium salts, and nitric acid. It is also possible nitrate the compound of formula (VI) without first protecting the aniline. In a particular embodiment, the compound of formula (VI) may be reacted with a nitrating agent at a temperature of between 0° C. and 50° C., between 5° C. and 50° C., between 10° C. and 50° C., between 15° C. and 50° C., between 20° C. and 50° C., between 22° C. and 50° C., between 24° C. and 45° C., between 25° C. and 45° C., between 27° C. and 45° C., between 28° C. and 45° C., between 28° C. and 44° C., between 28° C. and 43° C., between 28° C. and 42° C., between 30° C. and 45° C., between 30° C. and 44° C., between 30° C. and 43° C., or between 30° C. and 42° C.

The nitrated N-protected compound of formula (VI) may be deprotected using any method known to those skilled in the art. For example, an N-trifluoromethylcarbonyl-protected compound of formula (VI) may be deprotected by refluxing the N-protected compound in a solution of a strong acid such as $H_2SO_4$ or HCl. In addition, where R=H, the deprotection may be accomplished by refluxing the N-protected compound in the presence of a base, such as sodium hydroxide, potassium carbonate, or sodium acetate. Upon the completion of step D, the compound of formula (VI) of the present application provides a compound of formula (IV):

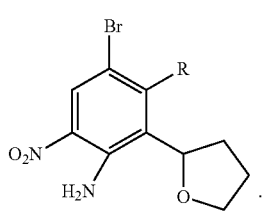

(IV)

In Step E, the compound of formula (IV) is subjected to a Suzuki-type coupling reaction with a boronic acid derivative of formula (III):

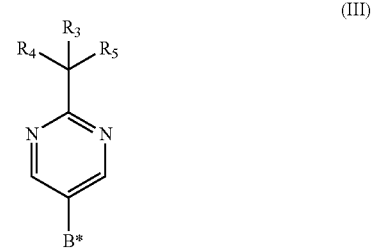

(III)

in the presence of a palladium catalyst, wherein each of $R_3$, $R_4$, and $R_5$ is independently an optionally substituted alkyl or an optionally protected hydroxyl group, and B* is

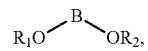

each of $R_1$ and $R_2$ being independently alkyl or H, or $OR_1$ and $OR_2$ together with the B atom to which they are attached forming an optionally substituted 5-, 6-, or 7-membered ring; or $BF_3X$, wherein X is any monovalent cation. The product of the Suzuki-type coupling reaction is subjected to catalytic hydrogenationto afford the compound of formula (II), wherein R is H or F, and each of $R_3$, $R_4$, and $R_5$ is independently an optionally substituted alkyl or an optionally protected hydroxyl group:

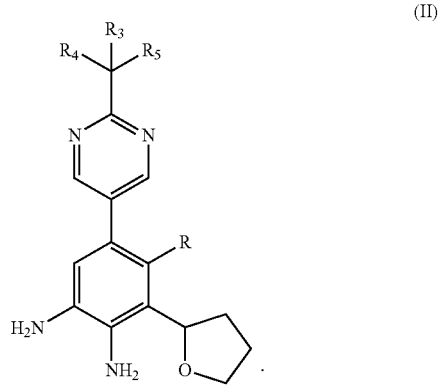

(II)

As used herein, the term boronic acid derivative refers boronic acids, boronate esters and, trifluoroborates. Boronic acids and boronate esters include any boron compound containing the group:

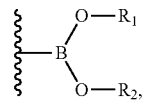

$R_1$ and $R_2$ being independently alkyl or H, or $OR_1$ and $OR_2$ together with the B atom to which they are attached forming an optionally substituted 5-, 6-, or 7-membered ring.

Examples of cyclic boronate esters include the following rings formed by OR$_1$, OR$_2$ and the B atom of compound of formula (III):

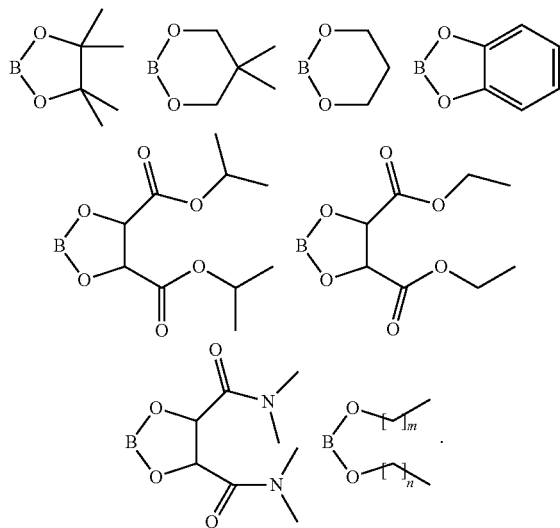

Compound 7 is a specific boronate ester. These examples of the boronic acid derivatives are but examples of possible variations on the substitution pattern of R$_1$ and R$_2$. The person skilled in the art can envision many additional possible modifications and all those modifications are contemplated in this application so long the modifications do not interfere with palladium catalyzed coupling reaction between the compounds of formulae (III) and (IV).

Trifluoroborates include any boron compound containing the group —BF$_3$X, wherein X is any monovalent cation. In some embodiments, X may be K$^+$, Na$^+$, Li$^+$, Rb$^+$, or Cs$^+$.

Each of R$_3$, R$_4$, and R$_5$ of the compounds of formulae (II) and (III) may independently be an optionally substituted alkyl or a hydroxy group wherein the hydroxy group may be protected with any of the protecting groups known to those skilled in the art. In one embodiment, each of R$_3$, R$_4$, and R$_5$ is a C$_1$-C$_6$ alkyl group or a hydroxy group. In a particular embodiment, each of R$_3$, R$_4$, and R$_5$ may independently be methyl, ethyl, propyl, isopropyl or hydroxy.

In one embodiment, the compound of formula (III) has the following structure:

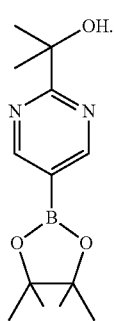

(7)

This application also contemplates using a pseudo-halide (e.g., triflate) instead of the bromo group in the compound of formula (IV):

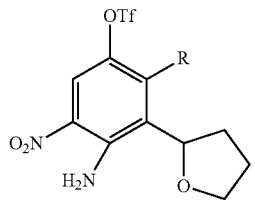

(IVa)

Any other leaving group that does not interfere with the coupling reaction may also be used. Other leaving groups include chloride, iodide, tosylate, and mesylate.

The palladium catalyst used in the Suzuki-type coupling reaction between compounds of formulae (III) and (IV) may be any suitable palladium catalyst known to those skilled in the art. Examples of Pd catalysts suitable for the Suzuki-type coupling reaction between compounds of formulae (III) and (IV) include Pd(II), Pd(I), and Pd(0) complexes. In one embodiment, the Pd(II) complex suitable for the present application has the generic formula PdX$_2$(phosphine)$_2$ wherein X is a monovalent negatively charged group such as a halide group and phosphine as used here refers to the class of compounds in which one, two, or three hydrogen atoms of the compound PH$_3$ is replaced with a corresponding number of groups such phenyl (Ph), cyclohexyl (Cy), tert-butyl (tBu), or isopropyl (iPr). Examples of phosphine ligands suitable for the Pd catalysts of the present application include di-tert-butylmethylphosphine, di-tert-butylneopentylphosphine, dicyclohexyl-(2-methylphenyl)phosphine, dicyclohexyl-(2,4,6-trimethylphenyl)phosphine, tricyclopentylphosphine, tert-butyldiphenylphosphine, cyclohexyldiphenylphosphine, tris(4-chlorophenyl)phosphine, benzyldiphenylphosphine, tri(m-tolyl)phosphine, tris(4-methoxyphenyl)phosphine, 1,3-bis(diphenylphosphino)propane (dppp), 1,2-bis(diphenylphosphino)ethane (dppe), 1,4-bis(diphenylphospino)butane (dppb), meso-2,4-bis(diphenylphosphino)pentane (mb-dpp), and 1,3-bis(diisopropylphosphino)propane (dippp). In another embodiment, Pd catalysts suitable for the Heck arylation reaction include PdCl$_2$(PPh$_3$)$_2$, PdCl$_2$(PCy$_3$)$_2$, PdCl$_2$(PiPr$_3$)$_2$, PdCl$_2$(PhCN)$_2$, Pd(N,N-dimethyl β-alaninate)$_2$, PdCl$_2${PR$_2$(Ph-R')}$_2$ wherein R is tert-butyl and R' is 4-dimethylamino group, bis(dibenzylideneacetone)palladium(II), palladium(II) acetate, PdCl$_2$(bis-hydrazone), [1,3-bis(2,6-diisopropylphenyl)imidazol-2-ylidene](3-chloropyridyl)palladium(II) dichloride, di(2-pyridyl)methanol palladium dichloride, 1,1'-bis(di tert-butylphosphino)ferrocene] dichloropalladium(II), 1,1'-bis(diphenylphosphino) ferrocene]dichloropalladium(II) (Pd(dppf)Cl$_2$), (NHC)Pd (allyl)Cl wherein NHC is an N-heterocyclic carbene such as N,N'-bis(2,6-diisopropylphenyl)imidazol)-2-ylidene, N,N'-bis(2,6-diisopropylphenyl)-4,5-dihydroimidazol)-2-ylidene, N,N'-bis(2,4,6-trimethylphenyl)-imidazole)-2-ylidene, and N,N'-bis tert-butyl-imidazol)-2-ylidene. In some embodiments, one or more Pd ligands may be tethered to a substrate such as a particle. Examples of such catalysts include (Ar'Ph$_2$P)$_2$PdCl$_2$ wherein the Ar' group is part of a polymer such that the catalyst is a polymeric palladium catalyst. In another embodiment, Pd(0) complexes useful in the present application include Pd(phosphine)$_4$ (e.g., Pd(PPh$_3$)$_4$, Pd(PCy$_3$)$_4$, Pd(PiPr$_3$)$_4$, Pd(tBu$_3$P)$_2$, and tris(dibenzylideneacetone)dipalladium(0). In still another embodiment, Pd(I) catalysts useful in the present application include Pd$_2$X$_2$ (phosphine)$_2$, wherein X is a monovalent anion, such as a halide. Examples of such Pd(I) catalysts include Pd$_2$Br$_2$ (tBu$_3$P)$_2$.

The product of the Suzuki coupling reaction is subjected to catalytic hydrogenation under the conditions set forth in step B.

In step F, the compound of formula (II) is treated with a compound of formula A or B to afford the benzimidazole compound of formula (I).

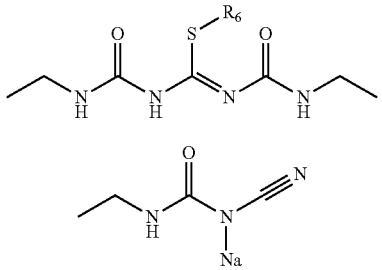

$R_6$ may be an optionally substituted alkyl group, benzyl, or p-nitrobenzyl. In particular embodiments, $R_6$ is methyl or ethyl.

In one embodiment, the compound of formula (I) has the following formula:

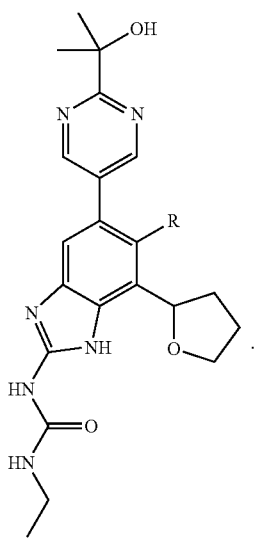

The compound of formula (Ia) contains one chiral center at C-2 of the tetrahydrofuryl ring. As such, the compound of formula (Ia) may be a racemic mixture or may contain an excess of one of the two enantiomers of the compound.

A racemic mixture of the compound of formula (Ia) may be enantiomerically enriched by using any method known to those skilled in the art. Examples of enantiomer enrichment methods known in the art include conversion of the enantiomers to diastereomers and using the different physical properties of diastereomers to separate the enantiomers, enriching one enantiomer. In some embodiments, the racemic mixture (or a mixture enriched in one enantiomer in which increasing the enantiomeric excess is desired) of the compound of formula (Ia) may be enantiomerically enriched using a preparative column chromatography suitable to isolate a pure or enantiomerically enriched enantiomer from a racemic mixture or from an enantiomerically enriched mixture in which higher enantiomeric enrichment is desired. In embodiments in which an enantiomeric mixture is enantiomerically enriched, the enantiomeric excess of one of the two enantiomers may be between about 5-100%, about 10-100%, about 20-100%, about 30-100%, about 40-100%, about 50-100%, about 60-100%, about 70-100%, about 80-100%, about 85-100%, about 90-100%, about 91-100%, about 92-100%, about 93-100%, about 94-100%, about 95-100%, about 96-100%, about 97-100%, about 98-100%, about 99-100%, or about 100%.

Compounds containing one or more protected hydroxy groups may be prepared using methods known to those skilled in the art. Examples of hydroxy protection schemes are described in Green, T. W. and Wuts, P. G. M., Protective Groups in Organic Synthesis, John Wiley & Sons, Inc., pp. 17-245 (1999).

The term "alkyl" as used herein refers to both straight and branched chain moieties of up to ten carbons. Examples of alkyl groups suitable for the present application include straight-chained and branched $C_{1-12}$ alkyl groups. As used herein, the term "short chain alkyl" is referred to an alkyl chain of up to 4 carbon atoms. As used herein, "a medium chain alkyl" is referred to an alkyl chain having 5-7 carbon atoms. Examples of alkyl groups include methyl, ethyl, propyl, isopropyl, butyl, sec-butyl, tert-butyl, 3-pentyl, hexyl and octyl groups, which may be optionally substituted.

Aryl groups suitable for the methods of the present application include $C_{6-14}$ aryl, preferably $C_{6-10}$ aryl. Typical $C_{6-10}$ aryl groups include phenyl, naphthyl, phenanthrenyl, anthracenyl, indenyl, azulenyl, biphenyl, biphenylenyl and fluorenyl groups.

The term "carbocycle" as used herein include cycloalkyl and partially saturated carbocyclic groups. Examples of cycloalkyl groups are $C_{3-7}$ cycloalkyl. Typical cycloalkyl groups include cyclopropyl, cyclobutyl, cyclopentyl, cyclohexyl and cycloheptyl.

The term "heterocycle" as used herein refers to a saturated or partially saturated 3-7 membered monocyclic, or 7-10 membered bicyclic ring system. The ring system of a heterocycle may consist of carbon atoms and from one to four heteroatoms selected from the group consisting of O, N, and S, wherein the nitrogen and sulfur heteroatoms may be oxidized, the nitrogen may be quaternized, and wherein the heterocyclic ring can be substituted on carbon or on a nitrogen atom if the resulting compound is stable.

Optional substituents on alkyl, aryl, saturated or unsaturated carbocycle, and saturated or unsaturated heterocycle include one or more of halo, $C_{1-6}$ haloalkyl, $C_{6-10}$ aryl, $C_{4-7}$ cycloalkyl, $C_{1-6}$ alkyl, $C_{2-6}$ alkenyl, $C_{2-6}$ alkynyl, $C_{6-10}$ aryl $(C_{1-6})$alkyl, $C_{6-10}$ aryl-$C_{2-6}$ alkenyl, $C_{6-10}$ aryl-$C_{2-6}$ alkynyl, $C_{1-6}$ hydroxyalkyl, nitro, amino, $C_{1-6}$ alkylamino, cyano, $C_{1-6}$ acylamino, hydroxy, sulfanyl, sulfonyl, sulfoxide, $C_{1-6}$ acyloxy, $C_{1-6}$ alkoxy, and carboxy.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the application. Isotopically-labeled forms of the compounds depicted herein, wherein one or more atoms are replaced by an atom having an atomic mass or mass number different from the atomic mass or mass number usually found in nature are also within the scope of this invention. Examples of isotopes that can be incorporated into compounds of the invention include isotopes of hydrogen, carbon, oxygen, and fluorine, such as $^2H$, $^3H$, $^{13}C$, $^{14}C$, $^{15}N$, $^{18}O$, and $^{17}O$. Such radio-labeled, and otherwise isotopically-labeled, compounds are useful, for example, as research tools or gyrase and/or topoisomerase IV inhibitors with improved therapeutic profile.

In one embodiment, compounds of formula (I) include compounds of formula (Ib)

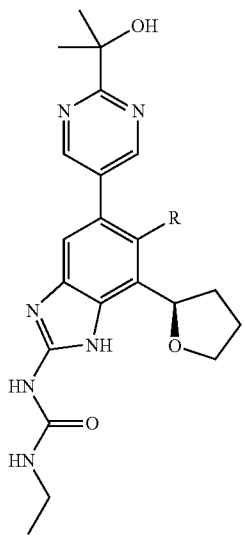
(Ib)

wherein R is H or F.

In another embodiment, compounds of formula (I) include compounds 12 and 23 set forth below:

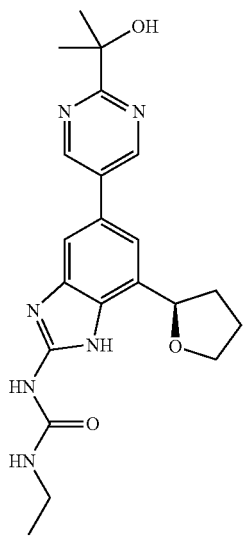
12

(R)-1-ethyl-3-(5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof; and

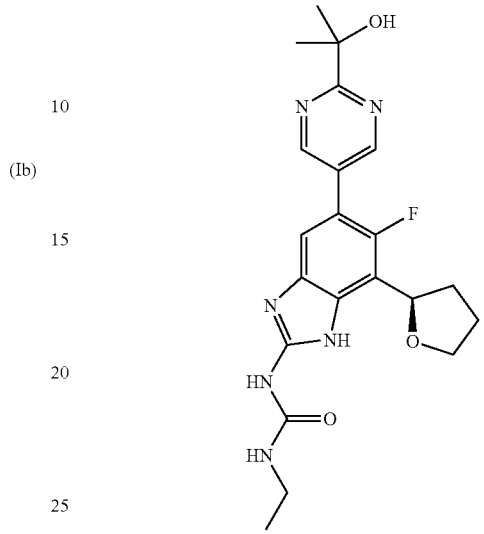
23

(R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof.

Though effective as a free base, the compound of formula (I) may be administered as pharmaceutically acceptable acid addition salts. The compounds of formula (I) may be converted to their corresponding acid addition salts using methods well known to those skilled in the art. Examples of non-toxic acid addition salts of the compound of formula (I) containing pharmaceutically acceptable anions include acetate, benzenesulfonate (also known as besylate), benzoate, bicarbonate, bitartrate, bromide, calcium edentate, camsylate, carbonate, chloride, citrate, dihydrochloride, edetate, edisylate, estolate, fumarate, gluceptate, gluconate, glutamate, glycollylarsaninate, hexylresorcinate, hydrabamine, hydrobromide, hydroxynaphthoate, iodide, isethionate, lactate, lactobionate, malate, maleate, mandelate, methanesulphonate (also known as mesylate), methylbromide, methylnitrate, methylsulfate, mucate, napsylate, nicotinate, nitrate, pamoate (embonate), pantothenate, phosphate, diphosphate, polygalacturonate, salicylate, stearate, subacetate, succinate, sulfate, bisulfate, tannate, tartrate, teoclate, p-toluenesulphonate (also known as tosylate), and triethiodide salts.

One embodiment of this application relates to a method of treating a bacterial infection in a mammal in need thereof, comprising administering to said mammal a therapeutically effective amount of a compound having the formula (I) or a pharmaceutically acceptable salt thereof.

In order that this application be more fully understood, the following examples are set forth. These examples are for the purpose of illustration only and are not to be construed as limiting the scope of the application in any way.

EXAMPLES

Example 1

Route to the Synthesis of Compounds 11, 12, and 13

Scheme 2 provides a method for preparing Compounds 11, 12, and 13.

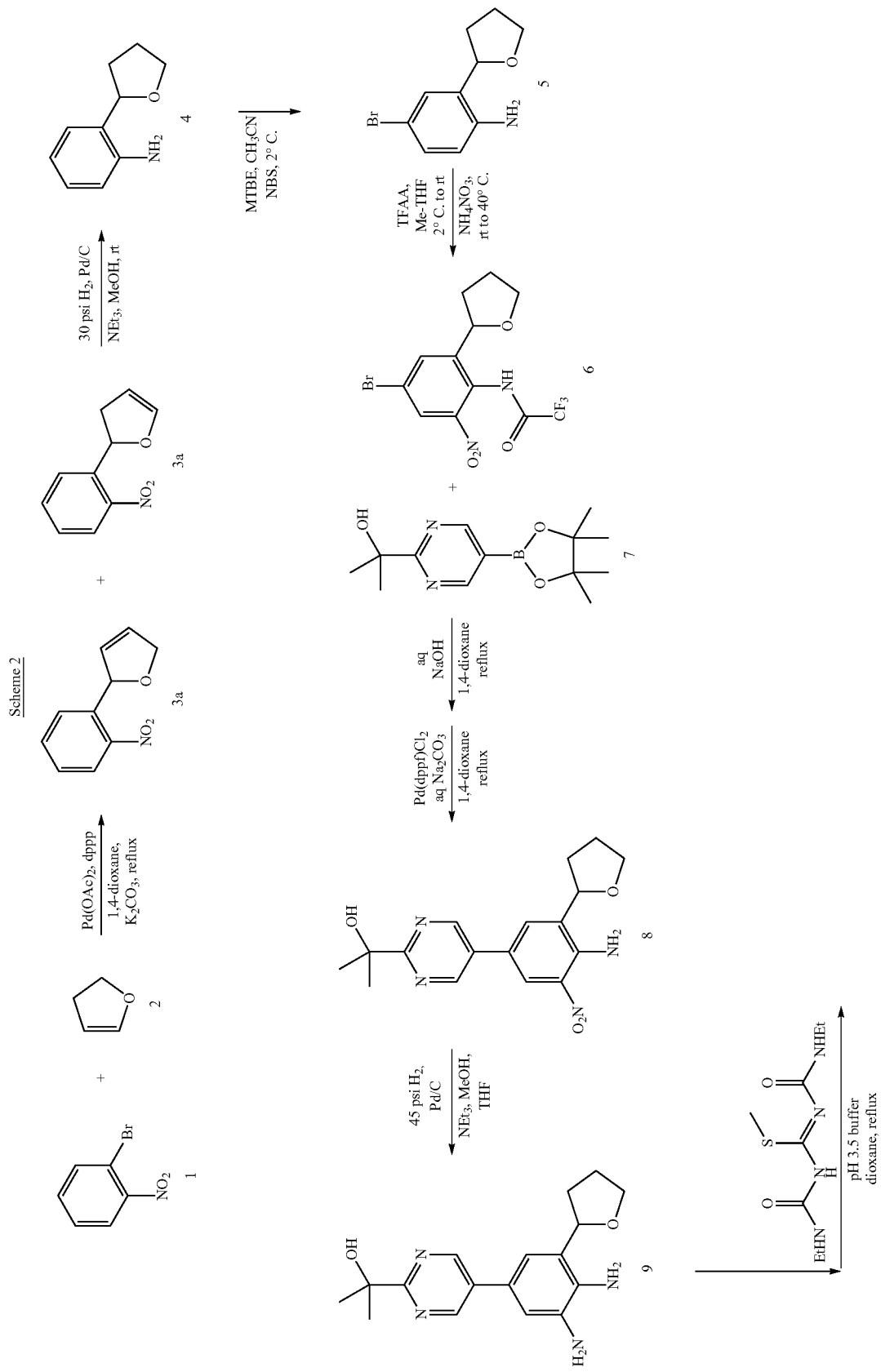

-continued
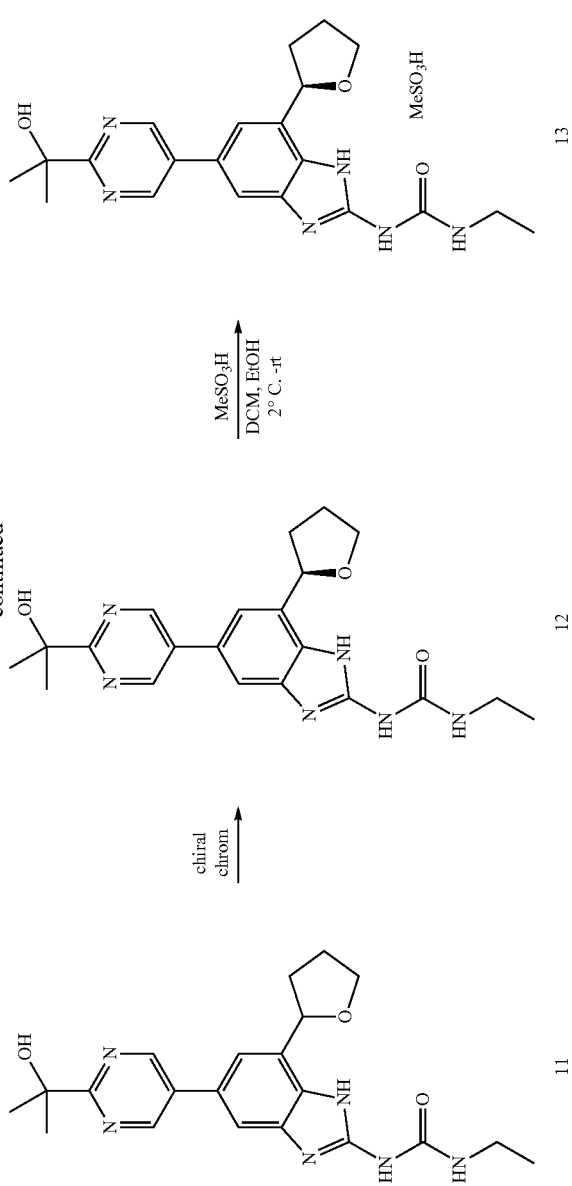

Example 1.a

Preparation of 2-(2-nitrophenyl)-2,5-dihydrofuran (3a) and 2-(2-nitrophenyl)-2,3-dihydrofuran (3b)

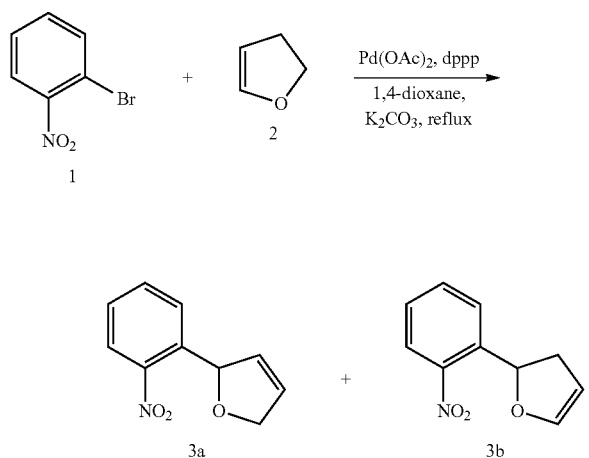

1-Bromo-2-nitro-benzene (1) (600 g, 99%, 2.941 mol, Alfa Aesar A11686), 1,3-bis(diphenylphosphino)propane (62.50 g, 97%, 147.0 mmol, Alfa Aesar A12931), 1,4-dioxane (2.970 L, Sigma-Aldrich 360481), potassium carbonate (812.9 g, 5.882 mol, JT-Baker 301201), and 2,3-dihydrofuran (2) (1.041 kg, 99%, 1.124 L, 14.70 mol, Aldrich 200018) were mixed in a reaction vessel. A stream of nitrogen was bubbled through the stirring mixture for 4 hrs, followed by addition of palladium (II) acetate (16.51 g, 73.52 mmol, Strem 461780) and continuation of deoxygenation for another 10 minutes. The reaction mixture was stirred at reflux under nitrogen overnight (NMR of a worked-up aliquot showed complete consumption of arylbromide). The reaction mixture was allowed to cool, diluted with hexane (1 L), filtered through a short plug of Florisil® (500 g, ~200 mesh), and eluted with EtOAc. The filtrate was concentrated under reduced pressure (2-(2-nitrophenyl)-2,3-dihydrofuran (3b) is volatile under high vacuum and may be somewhat unstable at room temperature) giving a mixture of (3a) and (3b) as a dark brown oil (654.0 g). The crude material was stored in the refrigerator and carried forward without further purification.

Example 1.a.1

Asymmetric Preparation of 2-(2-nitrophenyl)-2,5-dihydrofuran (3a) and 2-(2-nitrophenyl)-2,3-dihydrofuran (3b)

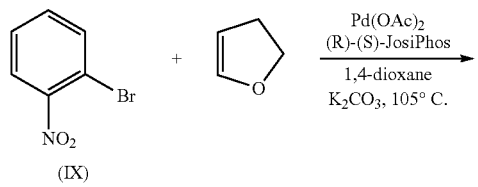

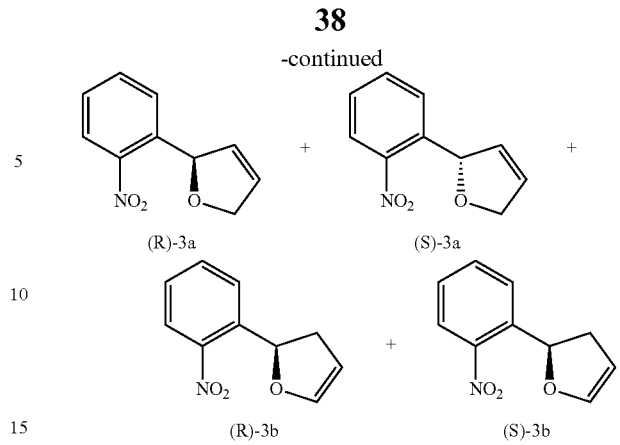

1-bromo-2-nitrobenzene (50.0 mg, 98%, 0.2426 mmol, Aldrich 365424), potassium carbonate (67.1 mg, 0.4852 mmol, JT-Baker 301201), (R)-(−)-1-[(S)-2-(diphenylphosphino)ferrocenyl]ethyldicyclohexylphosphine ethanol adduct ((R)—(S)-JosiPhos, 7.8 mg, 0.01213 mmol, Strem 261210), 2,3-dihydrofuran (1.0 mL, 99%, 13.08 mmol, Aldrich 200018), and 1,4-dioxane (0.98 mL) were mixed in a reaction tube. A stream of nitrogen was bubbled through the stirring mixture for 20 minutes, and then palladium (II) acetate (1.36 mg, 0.006065 mmol, Strem 461780) was added. The tube was sealed and the reaction mixture stirred at 105° C. overnight. HPLC of the crude reaction mixture showed nearly complete consumption of aryl bromide and formation of a 1:1 mixture of the 2-(2-nitrophenyl)-2,5-dihydrofuran (3a) and 2-(2-nitrophenyl)-2,3-dihydrofuran (3b). The reaction mixture was allowed to cool, diluted with hexane (2 mL), filtered, and rinsed with ethyl acetate. The filtrate was concentrated on a rotary evaporator to afford a brown oil (51 mg). The material was not placed under high vacuum due to volatility and stability concerns. The crude reaction mixture was determined to be a 1:1 mixture of (3a) and (3b) by $^1$HNMR analysis. The oil was purified by silica gel chromatography eluting with 0 to 38% EtOAc in hexane (or 0 to 100% $CH_2Cl_2$ in hexane) to afford pure samples of (3a) and (3b). Analytical data for these samples was as follows:

2-(2-nitrophenyl)-2,5-dihydrofuran (3a) was obtained as a yellow solid (97% HPLC purity, 97.0% ee): LCMS (C18 column eluting with 10-90% MeOH/water gradient from 3-5 minutes with formic acid modifier) M+1: 192.05 (3.40 min); HPLC retention time of 4.2 min (YMC ODS-AQ 150×3.0 mm column eluting with 10-90% $CH_3CN$/water gradient over 8 minutes with 0.1% TFA modifier and 1 mL/min flow rate); analytical chiral HPLC retention time of 7.4 min (major enantiomer) and 8.1 min (minor enantiomer) eluting with 10% iPrOH/hexane on a CHIRALCEL® OJ® 4.6×250 mm column with 1 mL/min flow rate at 30° C.; $^1$H NMR (300 MHz, $CDCl_3$) δ 8.02 (d, J=8.2 Hz, 1H), 7.73 (d, J=7.9 Hz, 1H), 7.64 (t, J=7.6 Hz, 1H), 7.45-7.38 (m, 1H), 6.37-6.30 (m, 1H), 6.11-6.06 (m, 1H), 6.04-5.98 (m, 1H), 5.02-4.83 (m, 2H) ppm; $^{13}$C NMR (75 MHz, $CDCl_3$) δ 146.97, 139.11, 133.95, 129.58, 128.10, 128.09, 126.78, 124.38, 84.28, 76.42 ppm; $^{13}$C DEPT NMR (75 MHz, $CDCl_3$) δ 133.95 (CH), 129.58 (CH), 128.10 (CH), 128.09 (CH), 126.78 (CH), 124.38 (CH), 84.28 (CH), 76.42 ($CH_2$) ppm.

2-(2-nitrophenyl)-2,3-dihydrofuran (3b) was obtained as a yellow oil (79-90% HPLC purity, 44.0% ee): LCMS (C18 column eluting with 10-90% MeOH/water gradient from 3-5 minutes with formic acid modifier) M+1: 192.05 (3.72 min); HPLC retention time of 4.8 min (YMC ODS-AQ 150×3.0 mm column eluting with 10-90% $CH_3CN$/water gradient over 8 minutes with 0.1% TFA modifier and 1 mL/min flow rate); analytical chiral HPLC retention time of 5.96 min (major enantiomer) and 6.35 min (minor enantiomer) eluting with 10% iPrOH/hexane on a CHIRALCEL® OJ® 4.6×250 mm column with 1 mL/min flow rate at 30° C.; $^1$H NMR (300 MHz, CDCl$_3$) δ 8.08 (d, J=8.2 Hz, 1H), 7.73 (d, J=7.8 Hz, 1H), 7.65 (t, J=7.6 Hz, 1H), 7.48-7.39 (m, 1H), 6.50 (q, J=2.4 Hz, 1H), 6.10 (dd, J=10.9, 7.4 Hz, 1H), 4.95 (q, J=2.5 Hz, 1H), 3.46-3.35 (m, 1H), 2.50-2.39 (m, 1H) ppm; $^{13}$C NMR (75 MHz, CDCl$_3$) δ 146.60, 144.98, 139.73, 133.93, 128.07, 127.11, 124.85, 99.29, 78.45, 38.29 ppm; $^{13}$C DEPT NMR (75 MHz, CDCl$_3$) δ 144.98 (CH), 133.93 (CH), 128.07 (CH), 127.11 (CH), 124.85 (CH), 99.29 (CH), 78.45 (CH), 38.29 (CH$_2$) ppm.

3a and 3b were carried through the reduction step to afford 2-tetrahydrofuran-2-yl-aniline (4) as set forth in Example 1.b (below). Analysis of this material revealed that both 3a and 3b were formed with the same major enantiomer, with an overall 70% ee. It is unknown whether the absolute stereochemistry of the major enantiomer was (R) or (S).

Example 1.b

Preparation of 2-tetrahydrofuran-2-yl-aniline (4)

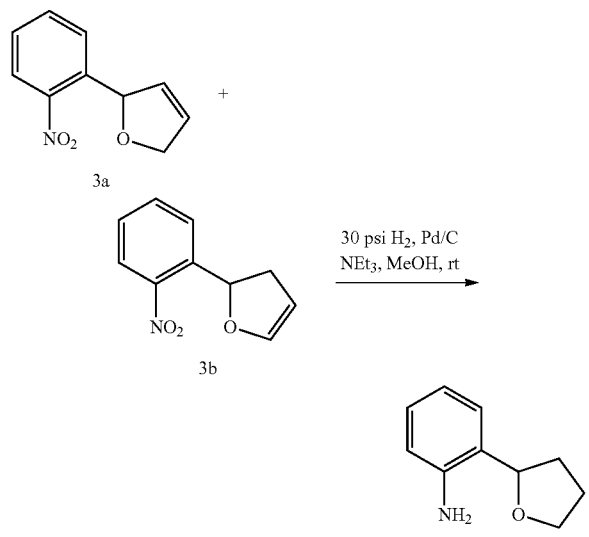

5% Palladium on carbon (16.3 g, 50% wet, 3.83 mmol, Aldrich 330116) was placed in a Parr bottle under nitrogen, followed by MeOH (100 mL, JT-Baker 909333). The crude mixture of 2-(2-nitrophenyl)-2,5-dihydrofuran and 2-(2-nitrophenyl)-2,3-dihydrofuran (3a & 3b) (163 g) dissolved in MeOH (389 mL) was added to the Parr bottle, followed by NEt$_3$ (237.6 mL, 1.705 mol, Sigma-Aldrich 471283). The bottle was placed on a Parr shaker and saturated with H$_2$. 30 psi H$_2$ was added and the bottle was shaken until starting material was completely consumed (LCMS and NMR showed complete reaction). The reaction mixture was purged with nitrogen, filtered through Celite™ and rinsed with EtOAc. The filtrate was concentrated on a rotary evaporator giving a brown oil. The reaction was repeated three more times on the same scale and the batches were combined for purification. The crude product was vacuum distilled (ca. 15 torr) collecting the distillate at 108-129° C. to give (4) as a clear faint yellow oil (427.9 g, average yield was 84%; 98% GCMS purity). LCMS (C18 column eluting with 10-90% CH$_3$CN/water gradient over 5 minutes with formic acid modifier) M+1: 163.95 (1.46 min). $^1$H NMR (300 MHz, CDCl$_3$) δ 7.15-7.04 (m, 2H), 6.77-6.62 (m, 2H), 4.85-4.77 (m, 1H), 4.18 (s, 2H), 4.12-4.02 (m, 1H), 3.94-3.85 (m, 1H), 2.25-1.95 (m, 4H) ppm.

Example 1.c

Preparation of 4-bromo-2-tetrahydrofuran-2-yl-aniline (5)

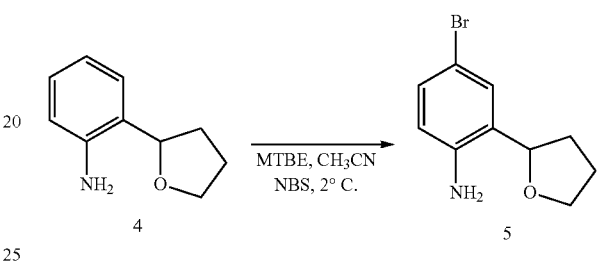

To a stirring solution of 2-tetrahydrofuran-2-yl-aniline (4) (53.45 g, 327.5 mmol) in methyl tert-butyl ether (MTBE, 641.4 mL) and acetonitrile (213.8 mL) cooled to 2° C. was added N-bromosuccinimide (NBS, 58.88 g, 99%, 327.5 mmol, Aldrich B81255) in 4 portions maintaining internal temperature below about 8° C. The reaction mixture was stirred while cooling with an ice-water bath for 30 minutes (NMR of a worked-up aliquot showed complete consumption of starting material). Aqueous 1 N Na$_2$S$_2$O$_3$ (330 mL) was added to the reaction mixture, removed the cold bath and stirred for 20 minutes. The mixture was diluted with EtOAc and the layers were separated. The organic phase was washed with saturated aqueous NaHCO$_3$ (2×), water, brine, dried over MgSO$_4$, filtered through a short plug of silica, eluted with EtOAc, and concentrated under reduced pressure to give (5) as a very dark amber oil (82.25 g, 77-94% HPLC purity). Carried forward without further purification. LCMS (C18 column eluting with 10-90% CH$_3$CN/water gradient over 5 minutes with formic acid modifier) M+1: 242.10 (2.89 min). $^1$H NMR (300 MHz, CDCl$_3$) δ 7.22 (d, J=2.3 Hz, 1H), 7.16 (dd, J=8.4, 2.3 Hz, 1H), 6.54 (d, J=8.4 Hz, 1H), 4.79-4.73 (m, 1H), 4.15 (s, 2H), 4.10-4.01 (m, 1H), 3.93-3.85 (m, 1H), 2.26-2.13 (m, 1H), 2.12-1.97 (m, 3H) ppm.

Example 1.d

Preparation of N-(4-bromo-2-nitro-6-tetrahydrofuran-2-yl-phenyl)-2,2,2-trifluoro-acetamide (6)

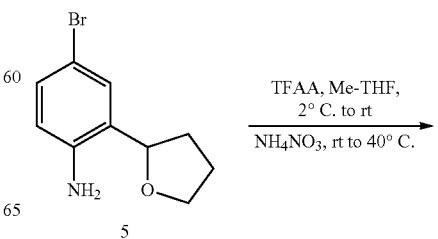

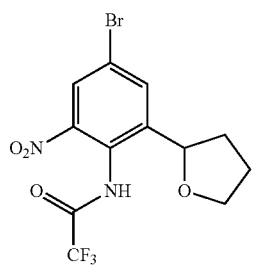

6

To trifluoroacetic anhydride (455.3 mL, 3.275 mol, Sigma-Aldrich 106232) stirring at 2° C. was slowly added 4-bromo-2-tetrahydrofuran-2-yl-aniline (5) (79.29 g, 327.5 mmol) as a thick oil via addition funnel over 15 minutes (reaction temperature rose to 14° C.). The remaining oil was rinsed into the reaction mixture with anhydrous 2-methyltetrahydrofuran (39.6 mL, Sigma-Aldrich 414247). The cold bath was removed and ammonium nitrate (34.08 g, 425.8 mmol, Aldrich 467758) was added. The reaction temperature rose to 40° C. over about 30 minutes at which time a cold water bath was used to control the exotherm and bring the reaction to room temperature. The cold bath was then removed and stirring continued for another 40 minutes (HPLC showed very little remaining un-nitrated material). The reaction mixture was slowly poured into a stirring mixture of crushed ice (800 g). The solid precipitate was collected by filtration, washed with water, saturated aqueous $NaHCO_3$ (to pH 8), water again, and hexane. The wet solid was dried first in a convection oven at 50° C. for several hours and then under reduced pressure in an oven at 40° C. overnight giving (6) as a light brown solid (77.86 g, 62% yield; 98% HPLC purity). LCMS (C18 column eluting with 10-90% $CH_3CN$/water gradient over 5 minutes with formic acid modifier) M+1: 383.19 (3.27 min). $^1$H NMR (300 MHz, $CDCl_3$) δ 9.81 (s, 1H), 8.08 (d, J=2.2 Hz, 1H), 7.73 (d, J=2.2 Hz, 1H), 4.88 (dd, J=9.0, 6.5 Hz, 1H), 4.17-4.08 (m, 1H), 4.03-3.95 (m, 1H), 2.45-2.34 (m, 1H), 2.17-2.06 (m, 2H), 1.96-1.83 (m, 1H) ppm.

Example 1.e

Preparation of 4-bromo-2-nitro-6-tetrahydrofuran-2-yl-aniline (6a)

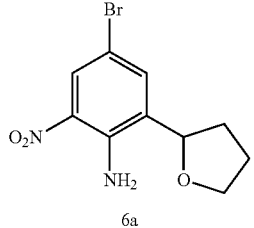

6a

N-(4-bromo-2-nitro-6-tetrahydrofuran-2-yl-phenyl)-2,2,2-trifluoro-acetamide (6) (54.00 g, 140.9 mmol) was dissolved in 1,4-dioxane (162 mL) and added aqueous 6 M NaOH (70.45 mL, 422.7 mmol, JT-Baker 567202). The reaction mixture was stirred at reflux for 2 days (HPLC showed complete conversion). The mixture was allowed to cool, diluted with MTBE (800 mL), and washed with water (2×200 mL), saturated aqueous $NH_4Cl$, water, and brine. The mixture was dried over $MgSO_4$, filtered, and concentrated under reduced pressure to give (6a) as a dark amber oil (40.96 g, 93% yield; overall 92% HPLC plus NMR purity). LCMS (C18 column eluting with 10-90% MeOH/water gradient from 3-5 minutes with formic acid modifier) M+1: 287.28 (3.44 min). $^1$H NMR (300 MHz, $CDCl_3$) δ 8.24 (d, J=2.4 Hz, 1H), 7.41 (d, J=2.3 Hz, 1H), 6.91 (s, 2H), 4.80 (t, J=7.2 Hz, 1H), 4.14-4.05 (m, 1H), 3.98-3.90 (m, 1H), 2.36-2.19 (m, 1H), 2.15-2.01 (m, 3H) ppm.

Example 1.f

Preparation of 2-[5-(4-amino-3-nitro-5-tetrahydrofuran-2-yl-phenyl)pyrimidin-2-yl]propan-2-ol (8)

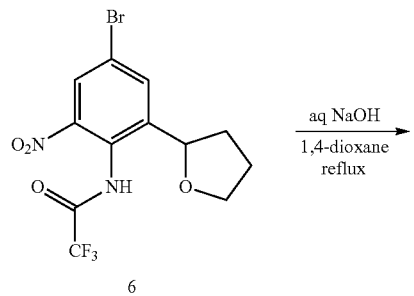

6a

+

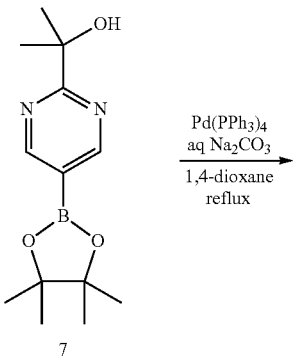

7

Example 1.g

Preparation of 2-[5-(3,4-diamino-5-tetrahydrofuran-2-yl-phenyl)pyrimidin-2-yl]propan-2-ol (9)

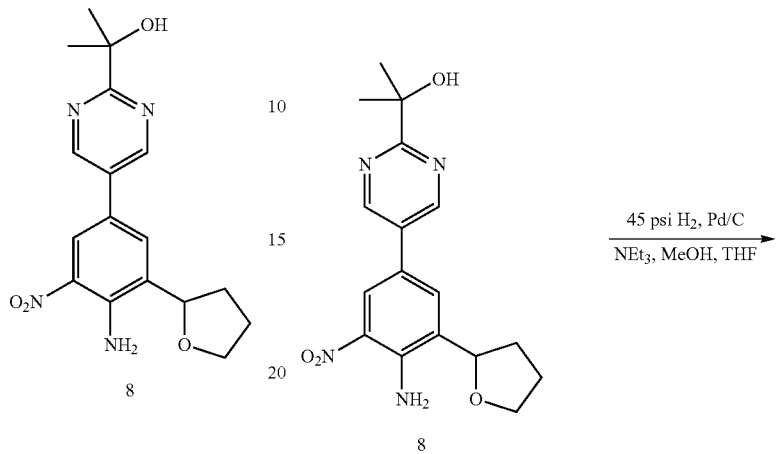

4-Bromo-2-nitro-6-tetrahydrofuran-2-yl-aniline (6a) (40.40 g, 92%, 129.5 mmol), 1,4-dioxane (260 mL, Sigma-Aldrich 360481), 2-[5-(4,4,5,5-tetramethyl-1,3,2-dioxaborolan-2-yl)pyrimidin-2-yl]propan-2-ol (7) (41.05 g, 155.4 mmol), and aqueous 2.7 M $Na_2CO_3$ (143.9 mL, 388.5 mmol) were mixed. A stream of nitrogen was bubbled through the stirring mixture for 1 hr, followed by addition of tetrakis(triphenylphosphine)palladium (0) (7.48 g, 6.47 mmol, Strem 462150). The reaction mixture was stirred at reflux for 2 hrs (HPLC showed complete reaction), allowed to cool, and diluted with EtOAc. The mixture was washed with water, saturated aqueous $NH_4Cl$, and brine, dried over $MgSO_4$, and filtered through a short plug of Florisil® eluting with EtOAc. The filtrate was concentrated under reduced pressure giving dark brown oil. The oil was dissolved in $CH_2Cl_2$ and eluted through a short plug of silica gel with $CH_2Cl_2$ and then EtOAc. The desired fraction was concentrated on a rotary evaporator until a precipitate formed giving thick brown slurry, which was triturated with MTBE. The solid was collected by filtration, washed with MTBE, and dried under high vacuum giving (8) as a yellow solid (35.14 g, 99+% HPLC purity). LCMS (C18 column eluting with 10-90% $CH_3CN$/water gradient over 5 minutes with formic acid modifier) M+1: 345.00 (2.69 min). $^1$H NMR (300 MHz, $CDCl_3$) δ 8.88 (s, 2H), 8.36 (d, J=2.2 Hz, 1H), 7.56 (d, J=2.1 Hz, 1H), 7.09 (s, 2H), 4.92 (t, J=7.2 Hz, 1H), 4.62 (s, 1H), 4.20-4.11 (m, 1H), 4.03-3.94 (m, 1H), 2.39-2.26 (m, 1H), 2.23-2.08 (m, 3H), 1.64 (s, 6H) ppm. The filtrate was concentrated and purified by ISCO silica gel chromatography eluting with 0 to 80% EtOAc/hexane giving a second crop of product (8) as an amber solid (4.46 g, 88% overall yield; 88% HPLC purity).

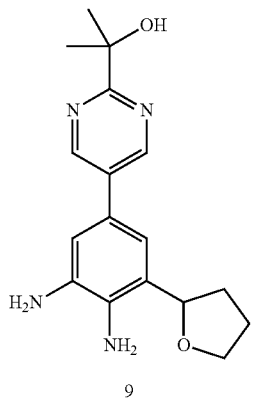

To a suspension of 2-[5-(4-amino-3-nitro-5-tetrahydrofuran-2-yl-phenyl)pyrimidin-2-yl]propan-2-ol (8) (30.10 g, 87.41 mmol) and THF (90 mL) in a Parr bottle under nitrogen was added a slurry of 5% palladium on carbon (3.01 g, 50% wet, 0.707 mmol, Aldrich 330116) in MeOH (90 mL, JT-Baker 909333), followed by $NEt_3$ (24.37 mL, 174.8 mmol, Sigma-Aldrich 471283). The vessel was placed on a Parr shaker and saturated with $H_2$. After adding 45 psi $H_2$, the vessel was shaken until consumption was complete (HPLC showed complete conversion). The reaction mixture was purged with nitrogen, filtered through Celite™ and rinsed with EtOAc. The filtrate was re-filtered through a 0.5 micron glass fiber filter paper sandwiched between two P5 papers, and concentrated under reduced pressure giving (9) as a light brown foam (28.96 g, 98% yield; 93% NMR purity). LCMS (C18 column eluting with 10-90% $CH_3CN$/water gradient over 5 minutes with formic acid modifier) M+1: 315.32 (1.54 min). $^1$H NMR (300 MHz, $CDCl_3$) δ 8.83 (s, 2H), 6.92 (d, J=1.8 Hz, 1H), 6.88 (d, J=1.8 Hz, 1H), 4.90 (dd, J=7.9, 6.2 Hz, 1H), 4.72 (s, 1H), 4.18 (s, 2H), 4.17-4.08 (m, 1H), 3.99-3.89 (m, 1H), 3.46 (s, 2H), 2.34-2.19 (m, 1H), 2.17-2.05 (m, 3H), 1.63 (s, 6H) ppm.

Example 1.h

Preparation of 1-ethyl-3-[5-[2-(1-hydroxy-1-methyl-ethyl)pyrimidin-5-yl]-7-tetrahydrofuran-2-yl-1H-benzimidazol-2-yl]urea (11)

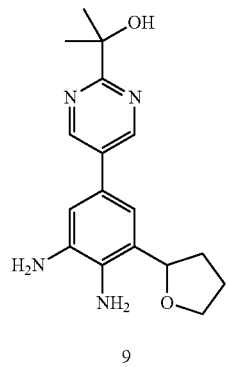

9

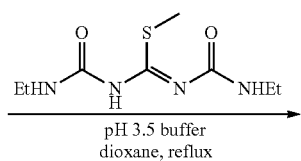

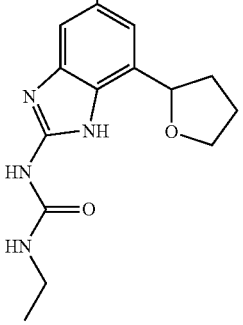

11

To a stirring solution of 2-[5-(3,4-diamino-5-tetrahydrofuran-2-yl-phenyl)pyrimidin-2-yl]propan-2-ol (9) (32.10 g, 102.1 mmol) in 1,4-dioxane (160.5 mL, Sigma-Aldrich 360481) was added pH 3.5 buffer (240.8 mL), prepared by dissolving NaOAc trihydrate (34.5 g) in 1N aqueous H$_2$SO$_4$ (240 mL). 1-Ethyl-3-(N-(ethylcarbamoyl)-C-methylsulfanyl-carbonimidoyl)urea (10) (28.46 g, 122.5 mmol, CB Research and Development) was added to the reaction mixture and stirred at reflux overnight (HPLC showed 99% consumption of starting diamine). The reaction mixture was cooled to room temperature and poured portion-wise (frothing) into a stirring solution of aqueous saturated NaHCO$_3$ (480 mL) and water (120 mL) giving pH 8-9. This was stirred for 30 minutes, the solid was collected by filtration, washed copiously with water to neutral pH, and then more sparingly with EtOH. The solid was dried under reduced pressure giving (11) as an off-white solid (34.48 g, 82% yield; 99.4% HPLC purity). LCMS (C18 column eluting with 10-90% CH$_3$CN/water gradient over 5 minutes with formic acid modifier) M+1: 411.41 (1.73 min). $^1$H NMR (300 MHz, MeOD) δ 9.02 (s, 2H), 7.62 (s, 1H), 7.37 (s, 1H), 5.31 (s, 1H), 4.23 (dd, J=14.5, 7.3 Hz, 1H), 4.01 (dd, J=15.0, 7.1 Hz, 1H), 3.38-3.28 (m, 2H), 2.58-2.46 (m, 1H), 2.16-2.05 (m, 2H), 2.02-1.88 (m, 1H), 1.63 (s, 6H), 1.22 (t, J=7.2 Hz, 3H) ppm.

Example 1.i

Chiral chromatographic isolation of 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea (12)

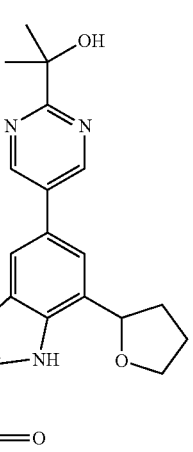

11 chiral chrom

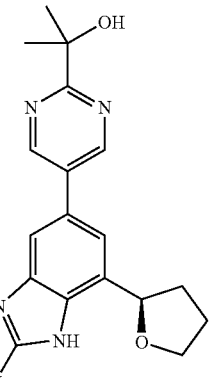

12

A racemic sample of 1-ethyl-3-[5-[2-(1-hydroxy-1-methyl-ethyl)pyrimidin-5-yl]-7-tetrahydrofuran-2-yl-1H-benzimidazol-2-yl]urea (11) (24.60 g) was resolved on a CHIRALPAK® IC® column (by Chiral Technologies) eluting with CH$_2$Cl$_2$/MeOH/TEA (60/40/0.1) at 35° C. giving the desired enantiomer (12) as a white solid (11.35 g, 45% yield; 99+% HPLC purity, 99+% ee). Analytical chiral HPLC retention time was 6.2 min (CHIRALPAK® IC® 4.6×250 mm column, 1 mL/min flow rate, 30° C.).

The structure and absolute stereochemistry of 12 were confirmed by single-crystal x-ray diffraction analysis. Single crystal diffraction data was acquired on a Bruker Apex II diffractometer equipped with sealed tube Cu K-alpha source (Cu Kα radiation, γ=1.54178 Å) and an Apex II CCD detector. A crystal with dimensions of ½×0.05×0.05 mm was selected, cleaned using mineral oil, mounted on a MicroMount and centered on a Bruker APEXII system. Three batches of 40 frames separated in reciprocal space were obtained to provide an orientation matrix and initial cell parameters. Final cell parameters were obtained and refined after data collection was completed based on the full data set. Based on systematic absences and intensities statistics the structure was solved and refined in acentric P2$_1$ space group.

A diffraction data set of reciprocal space was obtained to a resolution of 0.9 Å using 0.5° steps using 60 s exposure for each frame. Data were collected at 100 (2) K. Integration of intensities and refinement of cell parameters were accomplished using APEXII software. Observation of the crystal after data collection showed no signs of decomposition. As shown in FIG. 1, there are two symmetry independent molecules in the structure and both symmetry independent molecules are R isomers.

The data was collected, refined and reduced using the Apex II software. The structure was solved using the SHELXS97 (Sheldrick, 1990); program(s) and the structure refined using the SHELXL97 (Sheldrick, 1997) program. The crystal shows monoclinic cell with P2$_1$ space group. The lattice parameters are a=9.8423(4) Å, b=10.8426(3) Å, c=19.4441 (7) Å, β=102.966(3)°. Volume=2022.09(12) Å$^3$.

Example 1.j

Preparation of the methanesulfonic acid salt of 1-ethyl-3-[5-[2-(1-hydroxy-1-methyl-ethyl)pyrimidin-5-yl]-7-[(2R)-tetrahydrofuran-2-yl]-1H-benzimidazol-2-yl]-urea (13)

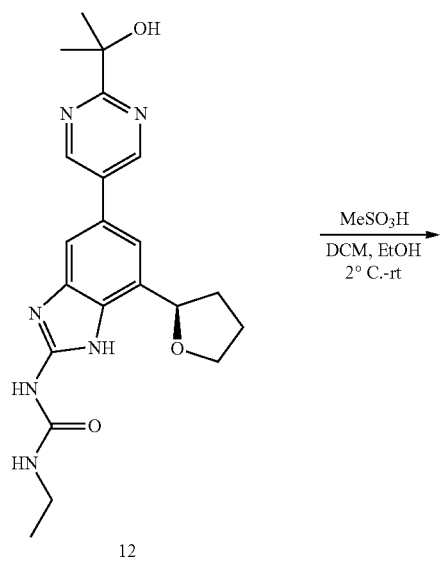

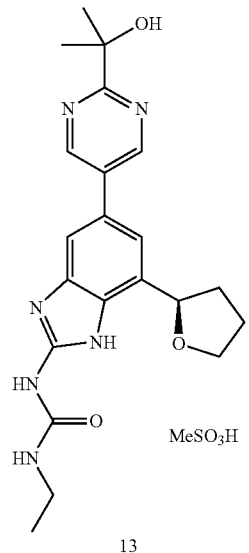

A stirring suspension of 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea (12) (9.32 g, 22.71 mmol) in absolute ethanol (93.2 mL) was cooled with an ice-water bath. Methanesulfonic acid (1.548 mL, 23.85 mmol, Sigma-Aldrich 471356) was added, removed cold bath and stirred at room temperature for 20 minutes. It was concentrated on a rotary evaporator at 35° C. to a thick slurry, diluted with EtOAc, collected the solid by filtration, washed with EtOAc, and dried under reduced pressure giving an initial crop of (13) as a white solid (8.10 g). The filtrate was concentrated on a rotary evaporator giving a yellowish glassy foam, which was dissolved in EtOH, concentrated to a solid slurry, triturated with EtOAc/Et$_2$O, and collected by filtration. The solid was washed with EtOAc/Et$_2$O, combined with the first crop, and dried under reduced pressure giving (13) as a white solid (9.89 g, 86% yield; 99+% HPLC purity, 99+% ee). Analytical chiral HPLC shows one enantiomer with retention time of 6.3 min eluting with CH$_2$Cl$_2$/MeOH/TEA (60/40/0.1) on a CHIRALPAK® IC® 4.6×250 mm column with 1 mL/min flow rate at 30° C. LCMS (C18 column eluting with 10-90% CH$_3$CN/water gradient over 5 minutes with formic acid modifier) M+1: 411.53 (1.74 min). $^1$H NMR (300 MHz, MeOD) δ 9.07 (s, 2H), 7.79 (s, 1H), 7.62 (s, 1H), 5.30 (t, J=7.3 Hz, 1H), 4.24 (dd, J=14.6, 7.3 Hz, 1H), 4.04 (dd, J=15.0, 7.6 Hz, 1H), 3.40-3.30 (m, 2H), 2.72 (s, 3H), 2.65-2.54 (m, 1H), 2.20-2.07 (m, 2H), 2.04-1.90 (m, 1H), 1.64 (s, 6H), 1.23 (t, J=7.2 Hz, 3H) ppm.

Example 1.1

1-pot deprotection/Suzuki procedure

Preparation of 2-[5-(4-amino-3-nitro-5-tetrahydrofuran-2-yl-phenyl)pyrimidin-2-yl]propan-2-ol (8)

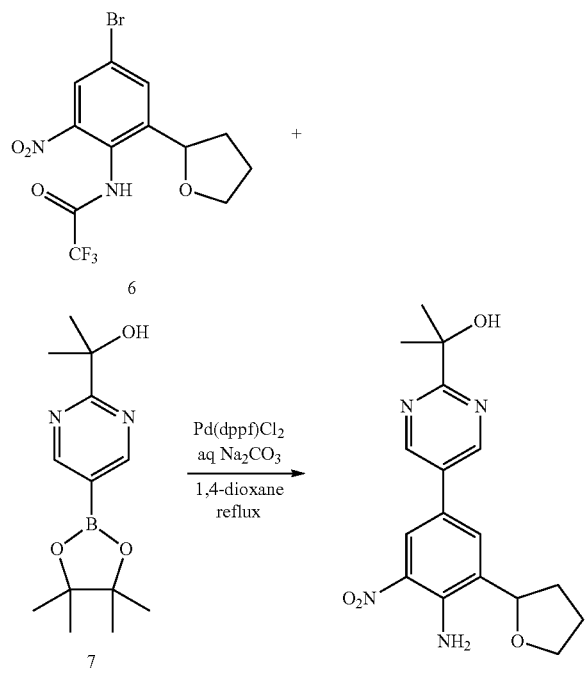

N-(4-Bromo-2-nitro-6-tetrahydrofuran-2-yl-phenyl)-2,2,2-trifluoro-acetamide (6) (19.00 g, 49.59 mmol), 2-[5-(4,4,5,5-tetramethyl-1,3,2-dioxaborolan-2-yl)pyrimidin-2-yl]propan-2-ol (7) (14.41 g, 54.55 mmol), aqueous 2.7 M sodium carbonate (73.48 mL, 198.4 mmol), and 1,4-dioxane (190 mL, Sigma-Aldrich 360481) were mixed. A stream of nitrogen was bubbled through the stirring mixture for 40 minutes, followed by addition of 1,1'-bis(diphenylphosphino)ferrocene dichloropalladium dichloromethane adduct (2.025 g, 2.480 mmol, Strem 460450). The reaction mixture was stirred at reflux under $N_2$ for 7 hrs, added another 50 mL of saturated aqueous sodium carbonate, and refluxed for another 16 hrs. The reaction mixture was allowed to cool, then diluted with EtOAc (500 mL) and water (200 mL). The layers were separated and the aqueous phase extracted with EtOAc (200 mL). The combined organic phase was washed with water (500 mL), brine (500 mL), dried over $Na_2SO_4$, filtered through a Florisil® plug, and concentrated on a rotary evaporator to give crude (8) as an orange oil. Purified by ISCO silica gel chromatography eluting with 20-90% EtOAc/hexane to give (8) as an orange solid (15.00 g, 81-88% purity). LCMS (C18 column eluting with 10-90% $CH_3CN$/water gradient over 5 minutes with formic acid modifier) M+1: 345.35 (2.68 min). $^1$H NMR (300 MHz, $CDCl_3$) δ 8.88 (s, 2H), 8.36 (d, J=2.2 Hz, 1H), 7.56 (d, J=2.1 Hz, 1H), 7.09 (s, 2H), 4.92 (t, J=7.2 Hz, 1H), 4.62 (s, 1H), 4.20-4.11 (m, 1H), 4.03-3.94 (m, 1H), 2.39-2.26 (m, 1H), 2.23-2.08 (m, 3H), 1.64 (s, 6H) ppm.

Example 2

Route to the Synthesis of Compounds 22, 23, and 24

Scheme 3 provides a method for preparing Compounds 22, 23 and 24.

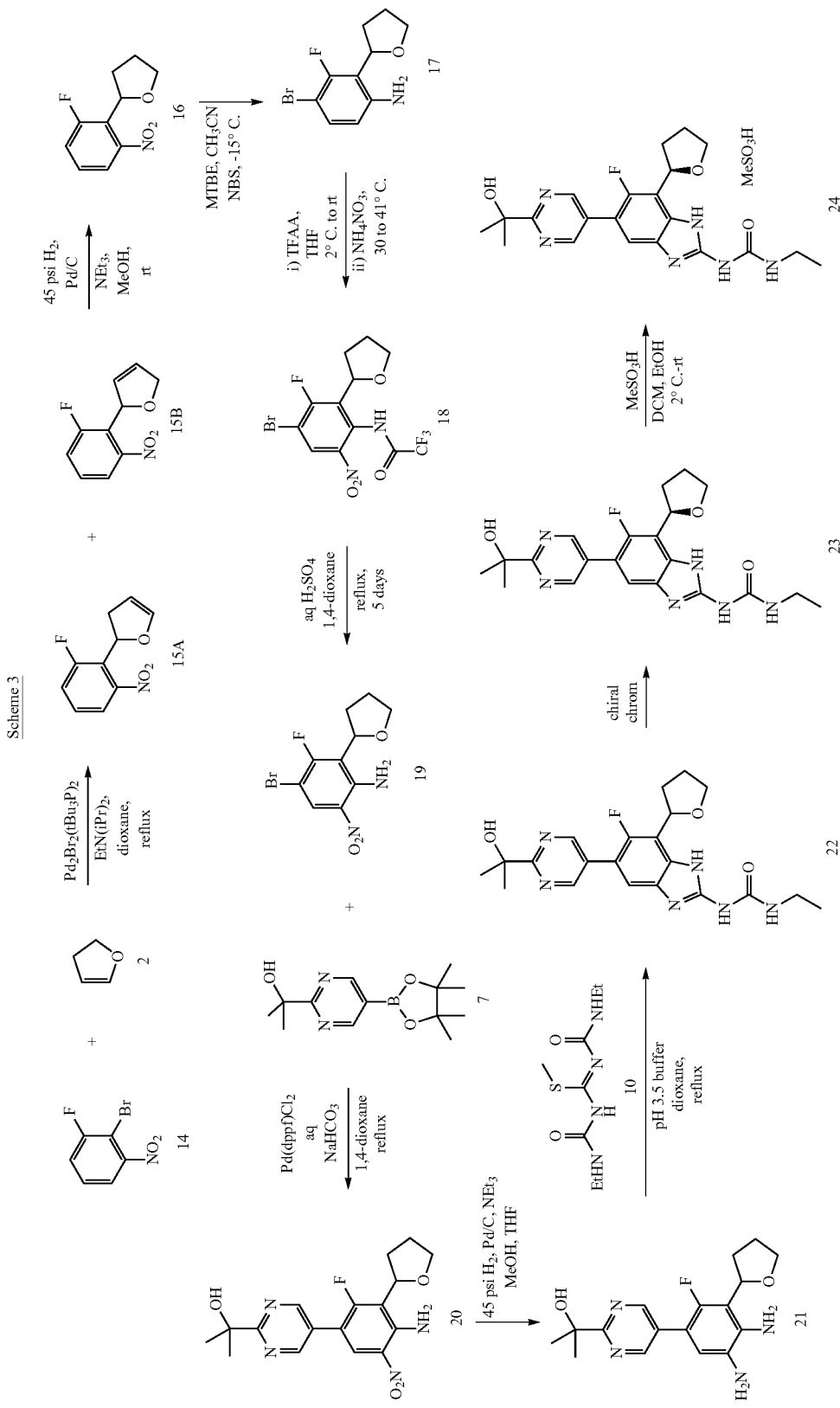

Example 2.a

Preparation of 2-(2-fluoro-6-nitro-phenyl)-2,3-dihydrofuran (15A) and 2-(2-fluoro-6-nitro-phenyl)-2,5-dihydrofuran (15B)

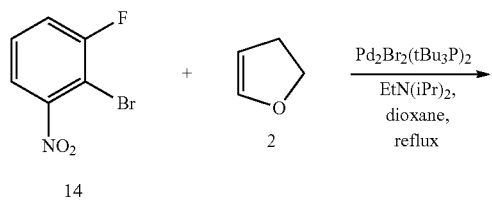

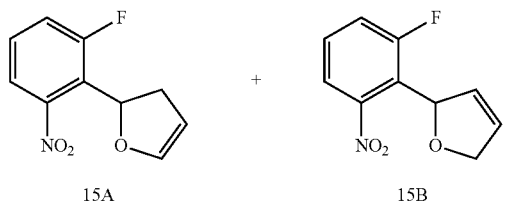

2-Bromo-1-fluoro-3-nitro-benzene (14) (200.3 g, 98%, 892.3 mmol, Bosche F6657), 1,4-dioxane (981.5 mL, Sigma-Aldrich 360481), and 2,3-dihydrofuran (2) (341.1 mL, 99%, 4.462 mol, Aldrich 200018) were charged in a reaction flask, followed by N,N-diisopropylethylamine (155.4 mL, 892.3 mmol, Sigma-Aldrich 550043) and bromo(tri-tert-butylphosphine)palladium(I) dimer (6.936 g, 8.923 mmol, Johnson Matthey C4099). The mixture was stirred at reflux for 2 hrs (HPLC showed 98% consumption of starting arylbromide). The reaction mixture was allowed to cool; the precipitate was removed by filtration, rinsed with EtOAc, and the filtrate concentrated in vacuo to a dark reddish brown semi-solid oil. The semi-solid oil was dissolved in $CH_2Cl_2$, eluted through a plug of silica with $CH_2Cl_2$, and concentrated in vacuo giving a mixture of 15A and 15B as a dark amber oil (291.3 g). The crude product was carried forward without further purification. The major product was 2-(2-fluoro-6-nitro-phenyl)-2,3-dihydrofuran (15A) (96%): LCMS (C18 column eluting with 10-90% $CH_3CN$/water gradient over 5 minutes with formic acid modifier) M+1: 210.23 (3.13 min); $^1H$ NMR (300 MHz, $CDCl_3$) δ 7.54 (dt, J=8.0, 1.2 Hz, 1H), 7.43 (td, J=8.2, 5.2 Hz, 1H), 7.32 (ddd, J=9.7, 8.3, 1.3 Hz, 1H), 6.33 (dd, J=4.9, 2.4 Hz, 1H), 5.80 (t, J=10.9 Hz, 1H), 5.06 (q, J=2.4 Hz, 1H), 3.18-3.07 (m, 1H), 2.94-2.82 (m, 1H) ppm. The minor product was 2-(2-fluoro-6-nitro-phenyl)-2,5-dihydrofuran (15B) (4%): GCMS (Agilent HP-5MS 30 m×250 μm×0.25 μm column heating at 60° C. for 2 min to 300° C. over 15 min with a 1 mL/min flow rate) M+1: 210 (11.95 min). $^1H$ NMR (300 MHz, $CDCl_3$) δ 7.47 (d, J=8.0 Hz, 1H), 7.43-7.34 (m, 1H), 7.30-7.23 (m, 1H), 6.21-6.15 (m, 1H), 6.11-6.06 (m, 1H), 5.97-5.91 (m, 1H), 4.89-4.73 (m, 2H) ppm.

Example 2.b

Preparation of 3-fluoro-2-tetrahydrofuran-2-yl-aniline (16)

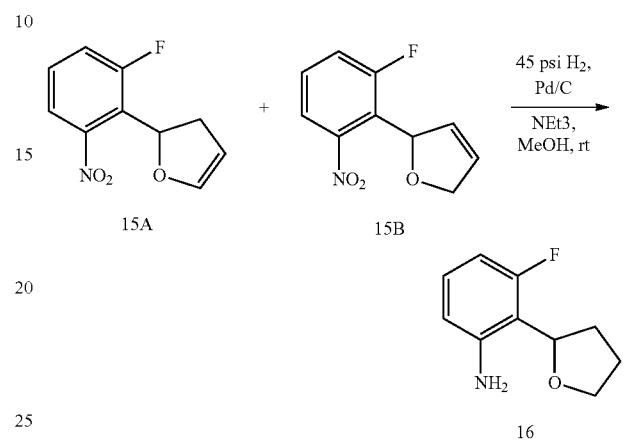

5% Palladium on carbon (37.3 g, 50% wet, 8.76 mmol, Aldrich 330116) was placed in a Parr bottle under nitrogen, followed by MeOH (70 mL, JT-Baker 909333). The crude mixture of 2-(2-fluoro-6-nitro-phenyl)-2,3-dihydrofuran and 2-(2-fluoro-6-nitro-phenyl)-2,5-dihydrofuran (15A & 15B) (186.6 g, 892.1 mmol) dissolved in MeOH (117 mL) was added to the Parr bottle, followed by $NEt_3$ (124.3 mL, 892.1 mmol, Sigma-Aldrich 471283). The bottle was placed on a Parr shaker and saturated with $H_2$. After adding 45 psi $H_2$, the reaction mixture was shaken until consumption of the starting material was complete (HPLC and LCMS showed complete reaction). The reaction mixture was purged with nitrogen, filtered through Celite™ and rinsed with EtOAc. The filtrate was concentrated on a rotary evaporator giving brown oil, which was dissolved in $Et_2O$ and washed with water (2×). The ether phase was extracted with aqueous 1 N HCl (5×250 mL), which was washed with $Et_2O$ (3×) and then basified with aqueous 6 N NaOH to pH 12-14. The basic aqueous phase was extracted with dichloromethane ($CH_2Cl_2$, 4×), and the combined organic extract was washed with saturated aqueous $NH_4Cl$, dried over $MgSO_4$, and filtered through a pad of silica eluting with $CH_2Cl_2$ to 25% EtOAc/hexane. The desired filtrate was concentrated under reduced pressure giving 16 as a light brown oil (121.8 g, 84% GCMS plus NMR purity). GCMS (Agilent HP-5MS 30 m×250 μm×0.25 μm column heating at 60° C. for 2 min to 300° C. over 15 min with a 1 mL/min flow rate) M+1: 182.0 (11.44 min). LCMS (C18 column eluting with 10-90% $CH_3CN$/water gradient over 5 minutes with formic acid modifier) M+1: 182.10 (2.61 min). $^1H$ NMR (300 MHz, $CDCl_3$) δ 6.97 (td, J=8.1, 6.3 Hz, 1H), 6.43-6.35 (m, 2H), 5.21-5.13 (m, 1H), 4.54 (s, 2H), 4.16-4.07 (m, 1H), 3.90-3.81 (m, 1H), 2.23-2.00 (m, 4H) ppm. Additional crops were obtained as follows: the combined ether phase was washed with saturated aqueous $NaHCO_3$, brine, dried over $Na_2SO_4$, decanted, and concentrated under reduced pressure. The oil was vacuum distilled (ca. 15 torr) collecting the distillate at 101-108° C. To a stirring solution of the distilled oil in EtOH (1 volume) at 2° C. was slowly added 5 M HCl (1 eq) in iPrOH. The resulting suspension was brought to room temperature, diluted with EtOAc (3 volumes, vol/vol), and stirred for 2 hrs. A white solid was collected by filtration, washed with EtOAc, and dried under reduced pressure giving a second crop of product as the HCl salt. The mother liquor was concentrated to a slurry, diluted with EtOAc and the solid collected by filtration, washed with EtOAc, and dried in vacuo giving the HCl salt as a third crop of the product. LCMS (C18 column eluting with 10-90% CH$_3$CN/water gradient over 5 minutes with formic acid modifier) M+1: 182.10 (2.58 min). $^1$H NMR (300 MHz, CDCl$_3$) δ 10.73 (br.s, 3H), 7.66 (d, J=8.1 Hz, 1H), 7.33 (td, J=8.2, 5.9 Hz, 1H), 7.13-7.05 (m, 1H), 5.26 (dd, J=9.0, 6.5 Hz, 1H), 4.38-4.28 (m, 1H), 4.00-3.91 (m, 1H), 2.59-2.46 (m, 1H), 2.30-1.95 (m, 3H) ppm. The overall yield from the three crops was 76%.

Example 2.c

Preparation of 4-bromo-3-fluoro-2-tetrahydrofuran-2-yl-aniline (17)

Hz, 1H), 6.30 (dd, J=8.7, 1.3 Hz, 1H), 5.19-5.12 (m, 1H), 4.58 (s, 2H), 4.16-4.07 (m, 1H), 3.90-3.81 (m, 1H), 2.23-1.99 (m, 4H) ppm.

Example 2.d

Preparation of N-(4-bromo-3-fluoro-6-nitro-2-tetrahydrofuran-2-yl-phenyl)-2,2,2-trifluoro-acetamide (18)

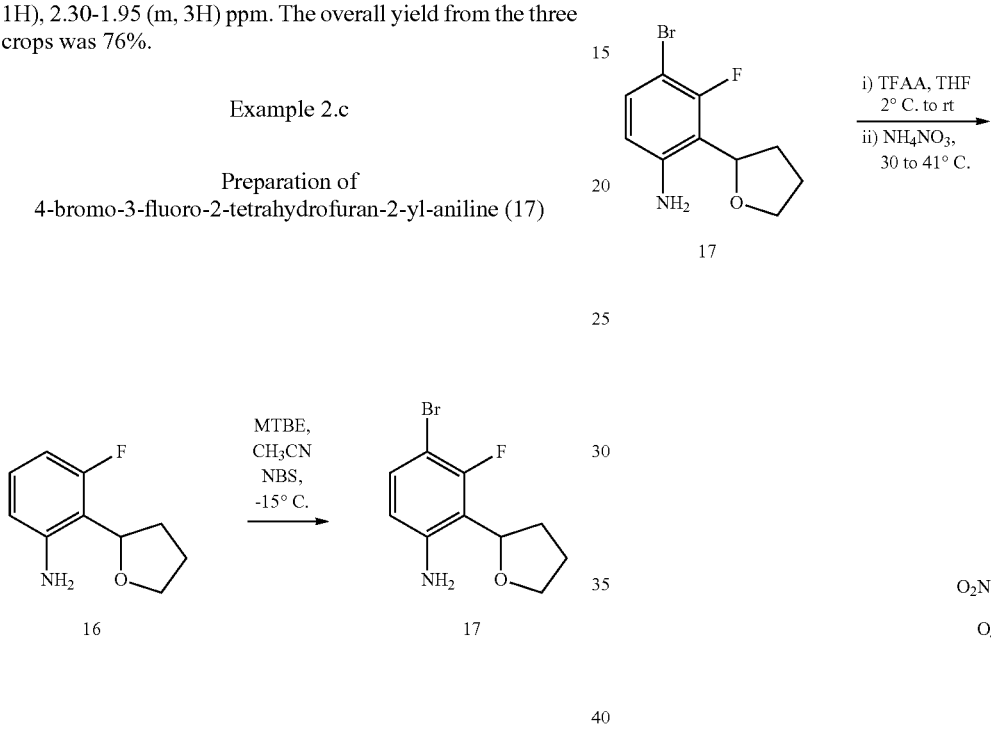

To a stirring solution of 3-fluoro-2-tetrahydrofuran-2-yl-aniline (16) (131.9 g, 92%, 669.7 mmol) in methyl tert-butyl ether (1.456 L) and acetonitrile (485 mL) cooled to −20° C. was added N-bromosuccinimide (120.4 g, 99%, 669.7 mmol, Aldrich B81255) in 3 portions maintaining a reaction temperature below about −15° C. After complete addition, stirring was continued at −15 to −10° C. for 30 minutes. $^1$H NMR of a worked-up aliquot showed 96% consumption of starting aniline. Another 4.82 g NBS was added to the reaction mixture and stirred at −10° C. for additional 30 minutes. Aqueous 1 N Na$_2$S$_2$O$_3$ (670 mL) was added to the reaction mixture. The cold bath was removed, the mixture stirred for 20 minutes, then diluted with EtOAc. The layers were separated. The organic phase was washed with saturated aqueous NaHCO$_3$ (2×), water, and brine, dried over Na$_2$SO$_4$, decanted, and concentrated under reduced pressure giving a dark amber oil. The residue was diluted with hexane and eluted through a short plug of silica with 25% EtOAc/hexane to 50% EtOAc/hexane. The desired filtrate was concentrated in vacuo giving 17 as dark amber oil (182.9 g, 90% yield; 86% NMR purity). LCMS (C18 column eluting with 10-90% AcN/water gradient over 5 minutes with formic acid modifier) M+1: 260.12 (3.20 min). $^1$H NMR (300 MHz, CDCl$_3$) δ 7.15 (dd, J=8.6, 7.6

To trifluoroacetic anhydride (565.3 mL, 4.067 mol, Sigma-Aldrich 106232) stirring at 2° C. was slowly added neat 4-bromo-3-fluoro-2-tetrahydrofuran-2-yl-aniline (17) (123.0 g, 86%, 406.7 mmol) as a thick oil via addition funnel over about 20 minutes (reaction temperature rose to 13° C.). The remaining oil was rinsed into the reaction mixture with anhydrous THF (35 mL). The cold bath was removed and the reaction was heated to 35° C., followed by portion-wise addition of NH$_4$NO$_3$ (4.88 g×20 portions, 1.22 mol, Sigma-Aldrich A7455) over 2.5 hrs maintaining the reaction temperature between 30 and 41° C. using an ice-water bath only as needed to control the exotherm. After complete addition the reaction mixture was stirred for another 10 minutes (HPLC showed reaction 99% complete). It was slowly poured into crushed ice (1.23 kg) and stirred for 1 hr to allow formation of a filterable solid precipitate, which was collected and washed with water, sparingly with saturated aqueous NaHCO$_3$, and water again (to pH 7). The product was dried in a convection oven overnight at 40° C. and then under reduced pressure in an oven at 50° C. overnight giving 18 as a beige solid (152.5 g, 90% yield; 96% HPLC purity). LCMS (C18 column eluting with 10-90% CH$_3$CN/water gradient over 5 minutes with formic acid modifier) M+1: 401.30 (3.41 min). $^1$H NMR (300 MHz, CDCl$_3$) δ 10.56 (s, 1H), 8.19 (d, J=6.6 Hz, 1H), 5.22

(dd, J=10.3, 6.4 Hz, 1H), 4.22 (dd, J=15.8, 7.2 Hz, 1H), 3.99 (dd, J=16.1, 7.5 Hz, 1H), 2.50-2.38 (m, 1H), 2.22-2.11 (m, 2H), 1.86-1.71 (m, 1H) ppm.

Example 2.e

Preparation of 4-bromo-3-fluoro-6-nitro-2-tetrahydrofuran-2-yl-aniline (19)

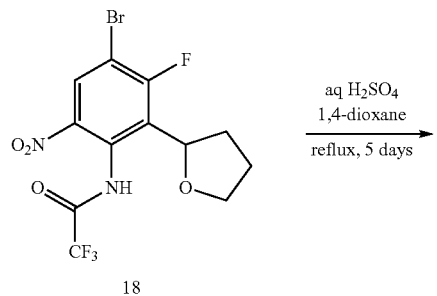

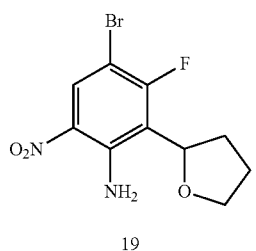

A reaction flask was charged with N-(4-bromo-3-fluoro-6-nitro-2-tetrahydrofuran-2-yl-phenyl)-2,2,2-trifluoro-acetamide (18) (242.3 g, 604.1 mmol), 1,4-dioxane (1.212 L), and aqueous 2 M sulfuric acid (362.4 mL, 724.9 mmol), and stirred at reflux for 5 days (HPLC showed 98% conversion). The reaction mixture was allowed to cool, diluted with EtOAc, neutralized with saturated aqueous NaHCO₃, separated the layers, and re-extracted the aqueous phase with EtOAc (2×). The combined organic phase was washed with brine (2×), dried over MgSO₄, filtered and concentrated in vacuo giving 19 as a greenish brown solid (181.7 g, 94% yield; 95% HPLC purity). The product was carried to the next step without further purification. LCMS (C18 column eluting with 10-90% CH₃CN/water gradient over 5 minutes with formic acid modifier) M+1: 305.20 (3.63 min). ¹H NMR (300 MHz, CDCl₃) δ 8.35 (d, J=7.3 Hz, 1H), 7.45 (s, 2H), 5.23-5.16 (m, 1H), 4.23-4.14 (m, 1H), 3.93-3.84 (m, 1H), 2.31-1.96 (m, 4H) ppm.

Example 2.f

Preparation of 2-[5-(4-amino-2-fluoro-5-nitro-3-tetrahydrofuran-2-yl-phenyl)pyrimidin-2-yl]propan-2-ol (20)

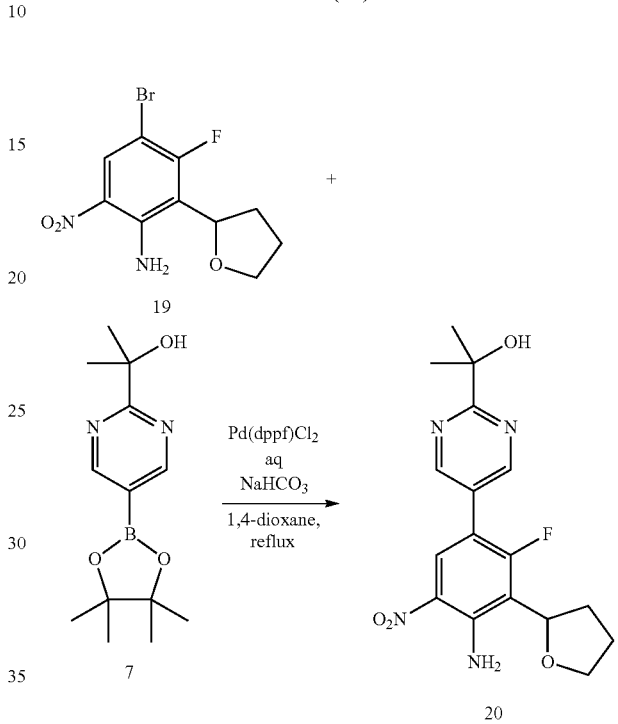

To a stirring solution of 4-bromo-3-fluoro-6-nitro-2-tetrahydrofuran-2-yl-aniline (19) (525.0 g, 1.721 mol, Bridge Organics Co.) in 1,4-dioxane (4.20 L, Sigma-Aldrich 360481) was added a 1.2 M aqueous solution of NaHCO₃ (4.302 L, 5.163 mol). A stream of nitrogen was bubbled through the stirring mixture for 2 hrs, followed by addition of 2-[5-(4,4,5,5-tetramethyl-1,3,2-dioxaborolan-2-yl)pyrimidin-2-yl]propan-2-ol (7) (545.4 g, 2.065 mol, Bridge Organics Co.) and 1,1'-bis(diphenylphosphino)ferrocene dichloropalladium dichloromethane adduct (42.16 g, 51.63 mmol, Strem 460450). The reaction mixture was stirred at reflux overnight, allowed to cool, diluted with EtOAc (8.4 L), and the layers were separated. The organic phase was washed with saturated aqueous NH₄Cl and then brine. The aqueous phase was re-extracted with EtOAc (4 L) and washed this organic extract with brine. The combined organic phase was dried over MgSO₄, filtered through a short plug of Florisil®, eluted with EtOAc, and the filtrate concentrated on a rotary evaporator giving a dark brown wet solid. This was dissolved in CH₂Cl₂, loaded on a pad of silica gel, eluted with hexane, then 25% EtOAc/hexane, and then 50% EtOAc/hexane. The desired filtrate was concentrated on a rotary evaporator to a thick suspension, and the solid was collected by filtration, triturated with MTBE, and dried in vacuo giving 20 as a bright yellow solid (55.8% yield, 90-97% HPLC purity). The filtrate was concentrated and the above purification was repeated giving a second crop of 20 as a bright yellow solid (19.7% yield). The filtrate was again concentrated giving a dark brown oil and this was loaded on a silica column with toluene and minimal CH$_2$Cl$_2$. It was eluted with EtOAc/hexane (0% to 50%). The desired fractions were concentrated to slurry and diluted with MTBE/hexane. The solid was collected by filtration and washed with minimal MTBE giving a third crop of 20 as a bright yellow solid (4.9% yield) with an overall yield of 80% from the three crops. LCMS (C18 column eluting with 10-90% CH$_3$CN/water gradient over 5 minutes with formic acid modifier) M+1: 363.48 (2.95 min). $^1$H NMR (300 MHz, CDCl$_3$) δ 8.84 (d, J=1.6 Hz, 2H), 8.27 (d, J=8.0 Hz, 1H), 7.62 (s, 2H), 5.31-5.24 (m, 1H), 4.63 (s, 1H), 4.27-4.18 (m, 1H), 3.97-3.87 (m, 1H), 2.33-2.05 (m, 4H), 1.64 (s, 6H) ppm.

Example 2.g

Preparation of 2-[5-(4,5-diamino-2-fluoro-3-tetrahydrofuran-2-yl-phenyl)pyrimidin-2-yl]propan-2-ol (21)

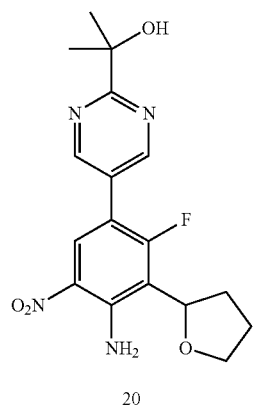

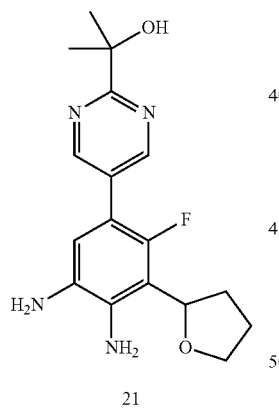

5% Palladium on carbon (14.21 g, 50% wet, 3.339 mmol, Aldrich 330116) was placed in a Parr bottle under nitrogen, followed by MeOH (242 mL, JT-Baker 909333) and NEt$_3$ (46.54 mL, 333.9 mmol, Sigma-Aldrich 471283). 2-[5-(4-Amino-2-fluoro-5-nitro-3-tetrahydrofuran-2-yl-phenyl)pyrimidin-2-yl]propan-2-ol (20) (121.0 g, 333.9 mmol) was dissolved in hot THF (360 mL), allowed to cool, added to the reaction mixture, and rinsed the residual amount of 20 with another portion of THF (124 mL). The bottle was placed on a Parr shaker and saturated with H$_2$. After adding 45 psi H$_2$, the bottle was shaken until consumption of 20 was complete (HPLC and LCMS showed complete reaction). The reaction mixture was purged with nitrogen, filtered through Celite™ and rinsed with EtOAc. It was re-filtered through paper (glass microfibre) and the filtrate concentrated in vacuo. The reaction was repeated three more times on the same scale and the batches were combined giving 21 as a brown solid (447 g, 99% yield; 93% HPLC purity). LCMS (C18 column eluting with 10-90% CH$_3$CN/water gradient over 5 minutes with formic acid modifier) M+1: 333.46 (1.79 min). $^1$H NMR (300 MHz, CDCl$_3$) δ 8.81 (d, J=1.4 Hz, 2H), 6.69 (d, J=7.3 Hz, 1H), 5.27-5.20 (m, 1H), 4.73 (s, 1H), 4.70 (s, 2H), 4.23-4.14 (m, 1H), 3.94-3.86 (m, 1H), 3.22 (s, 2H), 2.32-2.22 (m, 1H), 2.18-1.99 (m, 3H), 1.63 (s, 6H) ppm.

Example 2.h

Preparation of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22)

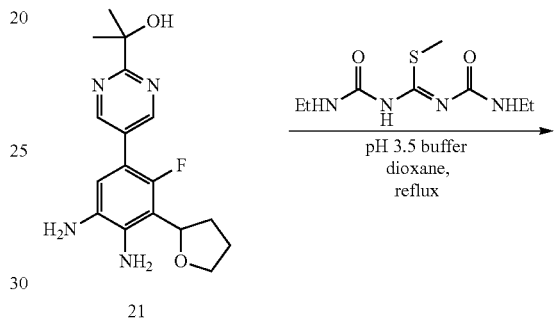

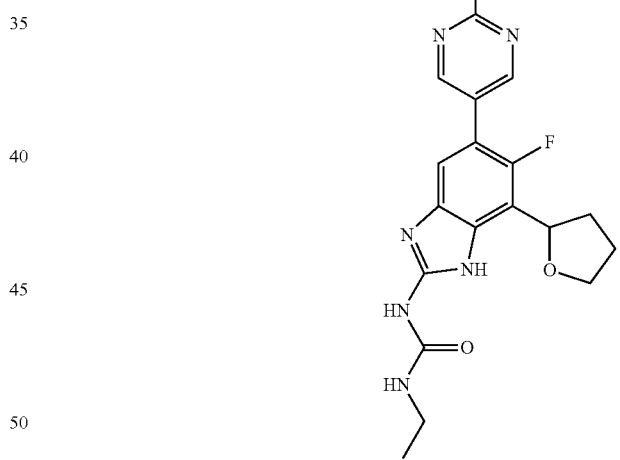

To a stirring suspension of 2-[5-(4,5-diamino-2-fluoro-3-tetrahydrofuran-2-yl-phenyl)pyrimidin-2-yl]propan-2-ol (21) (111.3 g, 334.9 mmol) and 1,4-dioxane (556.5 mL, Sigma-Aldrich 360481) was added 1-ethyl-3-(N-(ethylcarbamoyl)-C-methylsulfanyl-carbonimidoyl)urea (10) (93.36 g, 401.9 mmol, CB Research and Development) followed by a pH 3.5 buffer (1.113 L), prepared by dissolving NaOAc trihydrate (158.1 g) in 1N aqueous H$_2$SO$_4$ (1.100 L). The reaction mixture was stirred at reflux overnight (HPLC showed complete conversion), cooled to room temperature, and poured portion-wise (to minimize frothing) into a stirring solution of aqueous saturated NaHCO$_3$ (2.23 L) giving pH 8-9. The resulting mixture was stirred for 30 minutes, the solid was collected by filtration, washed copiously with water to neutral pH, and then more sparingly with EtOH. The solid was dried under reduced pressure giving 22 as an off-white yellowish solid (135.2 g, 94% yield; 99% HPLC purity). LCMS (C18 column eluting with 10-90% $CH_3CN$/water gradient over 5 minutes with formic acid modifier) M+1: 429.58 (2.03 min). $^1$H NMR (300 MHz, MeOD) δ 8.95 (d, J=1.6 Hz, 2H), 7.45 (d, J=6.5 Hz, 1H), 5.38 (br.s, 1H), 4.27 (dd, J=14.9, 7.1 Hz, 1H), 4.01 (dd, J=15.1, 7.0 Hz, 1H), 3.37-3.29 (m, 2H), 2.55 (br.s, 1H), 2.19-2.07 (m, 2H), 2.02-1.82 (br.s, 1H), 1.63 (s, 6H), 1.21 (t, J=7.2 Hz, 3H) ppm.

Example 2.i

Chiral chromatographic isolation of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23)

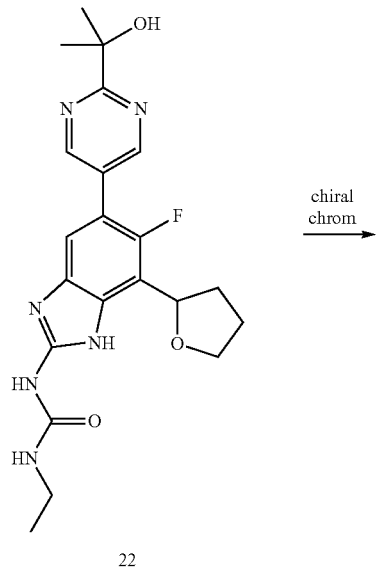

A racemic sample of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22) (133.60 g) was resolved on a CHIRALPAK® IC® column (by Chiral Technologies) eluting with $CH_2Cl_2$/MeOH/TEA (60/40/0.1) at 25° C. giving the desired enantiomer 23 as an off-white solid (66.8 g, 45% yield; 99.8% HPLC purity, 99+% ee). Analytical chiral HPLC retention time was 7.7 min (CHIRALPAK® IC® 4.6×250 mm column, 1 mL/min flow rate, 30° C.). The solid was suspended in 2:1 EtOH/$Et_2O$ (5 volumes), stirred for 10 minutes, collected by filtration, washed with 2:1 EtOH/$Et_2O$, and dried under reduced pressure giving a white solid (60.6 g).

The structure and absolute stereochemistry of 23 were confirmed by single-crystal x-ray diffraction analysis. Single crystal diffraction data was acquired on a Broker Apex II diffractometer equipped with sealed tube Cu K-alpha source (Cu Kα radiation, γ=1.54178 Å) and an Apex II CCD detector. A crystal with dimensions of 0.15×0.15×0.10 mm was selected, cleaned using mineral oil, mounted on a MicroMount and centered on a Bruker APEXII system. Three batches of 40 frames separated in reciprocal space were obtained to provide an orientation matrix and initial cell parameters. Final cell parameters were obtained and refined after data collection was completed based on the full data set. Based on systematic absences and intensities statistics the structure was solved and refined in acentric $P2_1$ space group.

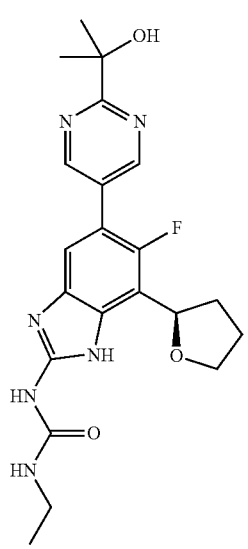

Figure 2:
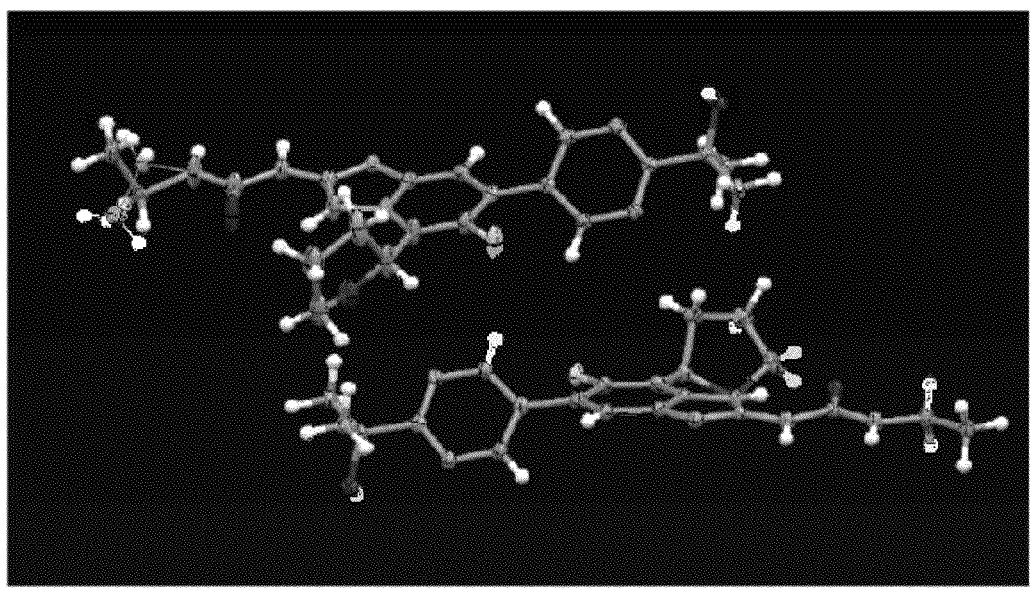
FIG. 2 is a thermal ellipsoid plot of two symmetry independent molecules of compound 23.

A diffraction data set of reciprocal space was obtained to a resolution of 0.85 Å using 0.5° steps using 30 s exposure for each frame. Data were collected at 100 (2) K. Integration of intensities and refinement of cell parameters were accomplished using APEXII software. Observation of the crystal after data collection showed no signs of decomposition. As shown in FIG. 2, there are two symmetry independent molecules in the structure and both symmetry independent molecules are R isomers.

The data was collected, refined and reduced using the Apex II software. The structure was solved using the SHELXS97 (Sheldrick, 1990); program(s) and the structure refined using the SHELXL97 (Sheldrick, 1997) program. The crystal shows monoclinic cell with $P2_1$ space group. The lattice parameters are a=9.9016(2) Å, b=10.9184(2) Å, c=19.2975 (4) Å, β=102.826(1)°. Volume=2034.19(7) Å$^3$.

Example 2.j

Preparation of the methanesulfonic acid salt 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (24)

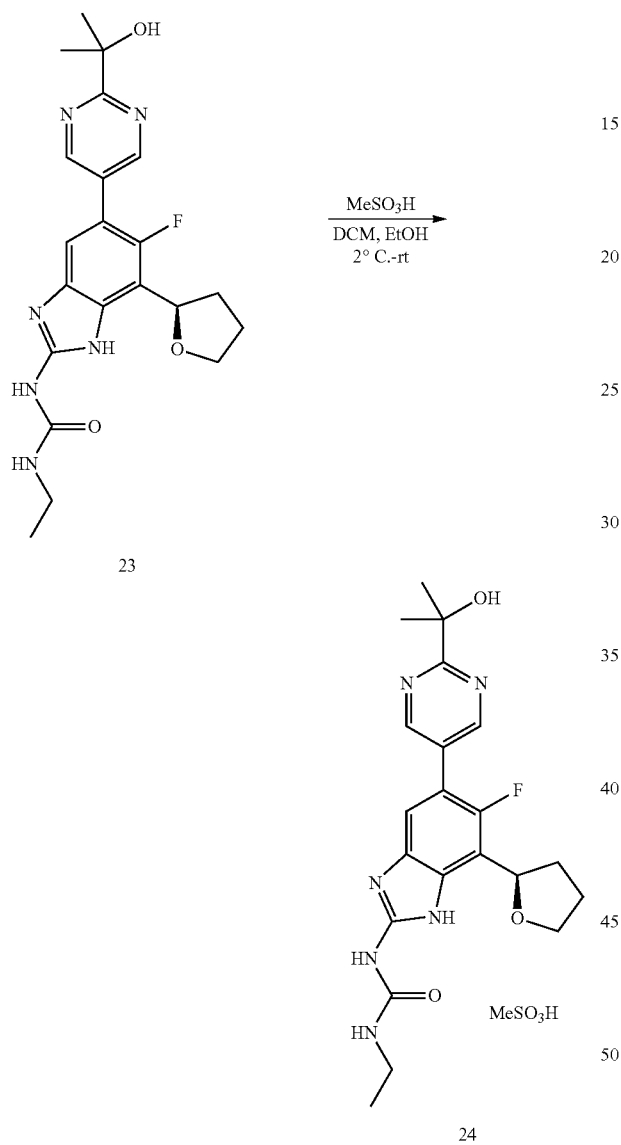

To a stirring suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (15.05 g, 35.13 mmol) in dichloromethane (60 mL, J. T. Baker 931533) and absolute ethanol (15 mL, Pharmco-AAPER 111000200) was added methanesulfonic acid (2.392 mL, 36.89 mmol, Sigma-Aldrich 471356). Stirred at room temperature until a clear solution was observed. Added heptane (300 mL) slowly over about 1 hr and collected the solid precipitate by filtration (using a Whatman qualitative #3 paper on top of a Whatman GF/F glass microfibre paper). Dried under reduced pressure in a vacuum oven (desiccated with calcium sulfate and potassium hydroxide) overnight at 40° C. giving 24 as a white solid (13.46 g, 99+% HPLC purity, 99+% ee). Analytical chiral HPLC shows one enantiomer with retention time of 8.6 min eluting with $CH_2Cl_2$/MeOH/TEA (60/40/0.1) on a CHIRALPAK® IC® 4.6×250 mm column with 1 mL/min flow rate at 30° C. A second crop of white solid product 24 (4.36 g, 98% HPLC purity, 99+% ee) was obtained from the filtrate. LCMS (C18 column eluting with 10-90% $CH_3CN$/water gradient over 5 minutes with formic acid modifier) M+1: 429.58 (2.03 min). $^1$H NMR (300 MHz, MeOD) δ 9.00 (d, J=1.6 Hz, 2H), 7.67 (d, J=6.1 Hz, 1H), 5.39 (t, J=7.7 Hz, 1H), 4.30 (dd, J=14.9, 6.9 Hz, 1H), 4.03 (dd, J=14.8, 7.7 Hz, 1H), 3.40-3.31 (m, 2H), 2.72 (s, 3H), 2.70-2.60 (m, 1H), 2.21-2.08 (m, 2H), 1.98-1.84 (m, 1H), 1.65 (s, 6H), 1.22 (t, J=7.2 Hz, 3H) ppm.

What is claimed is:
1. A method for preparing a compound of formula (I)

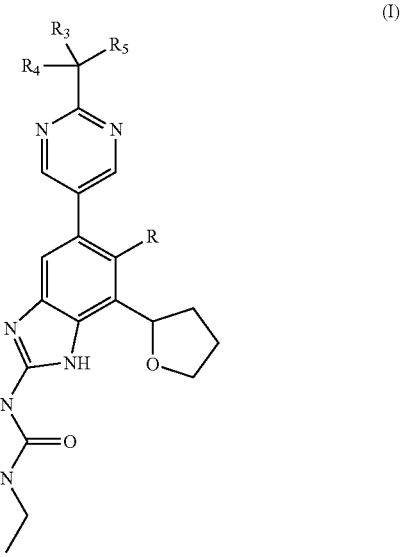

or a pharmaceutically acceptable salt thereof, wherein R is H or F; and each of $R_3$, $R_4$, and $R_5$ is independently an optionally substituted alkyl or an optionally protected hydroxyl group;

comprising providing a phenylpyrimidine compound of formula (II)

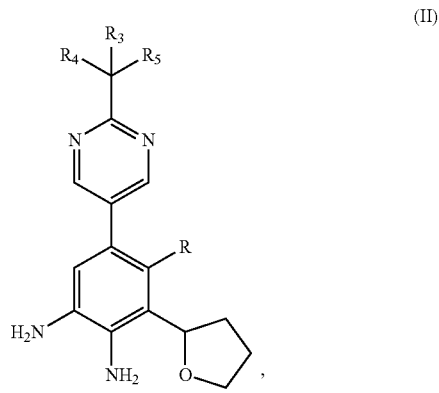

wherein R is H or F, and each of $R_3$, $R_4$, and $R_5$ is independently an optionally substituted alkyl or an optionally protected hydroxyl group;

and reacting the phenylpyrimidine compound of formula (II) with a urea derivative of formula A or B:

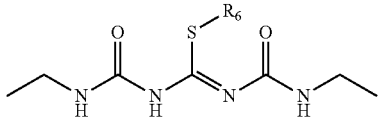

A

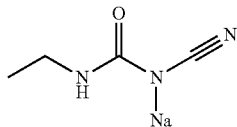

B wherein $R_6$ is an optionally substituted alkyl, optionally substituted aryl, optionally substituted saturated or unsaturated carbocycle, or optionally substituted saturated or unsaturated heterocycle; to provide a compound of formula (I); and optionally reacting the compound of formula (I) with a suitable acid to provide a pharmaceutically acceptable salt of the compound of formula (I).

2. The method of claim 1, wherein $R_6$ is methyl, ethyl, benzyl, or p-nitrobenzyl.

3. The method of claim 1, wherein said reaction is conducted in a mixture of dioxane and a buffer at 75° C. to 125° C.

4. The method of claim 3, wherein the buffer is a pH 3.5 buffer and the reaction is conducted at reflux.

5. The method of claim 1, wherein said providing a phenylpyrimidine compound of formula (II) comprises providing a phenyltetrahydrofuran derivative of formula (IV)

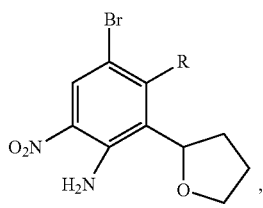

(IV)

wherein R is H or F; and reacting the phenyltetrahydrofuran compound of formula (IV) with a boronic acid derivative of formula (III)

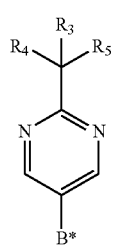

(III)

wherein each of $R_3$, $R_4$, and $R_5$ is independently an optionally substituted alkyl or an optionally protected hydroxyl group, and B* is

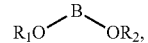

each of $R_1$ and $R_2$ being independently alkyl or H, or $OR_1$ and $OR_2$ together with the B atom to which they are attached forming an optionally substituted 5-, 6-, or 7-membered ring, or $BF_3X$, X being any monovalent cation, in the presence of a palladium catalyst in a polar solvent to provide a phenylpyrimidine compound of formula (V),

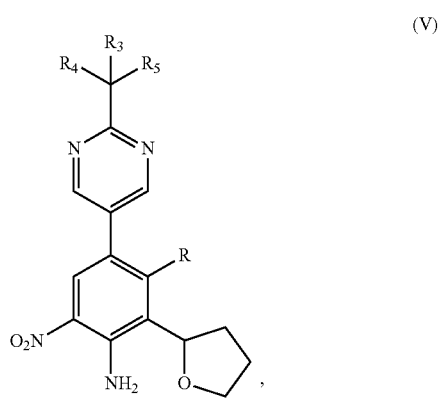

(V)

wherein R is H or F, and each of $R_3$, $R_4$, and $R_5$ is independently an optionally substituted alkyl or an optionally protected hydroxyl group; and treating the phenylpyrimidine compound of formula (V) with a suitable reducing agent to afford the phenylpyrimidine compound of formula (II).

6. The method of claim 5, wherein B* is selected from the group consisting of

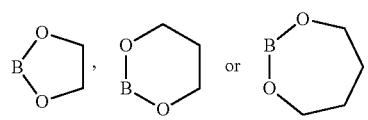

wherein each of the carbon atoms of the ring may be unsubstituted or substituted with one or two methyl or ethyl groups.

7. The method of claim 6, wherein B* is

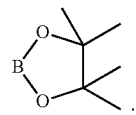

8. The method of claim 5, wherein said providing a phenyltetrahydrofuran compound of formula (IV) comprises providing a compound of formula (VI)

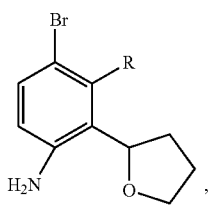

wherein R is H or F;
and nitrating the compound of formula (VI) with a suitable nitrating agent to afford the phenyltetrahydrofuran compound of formula (IV).

9. The method of claim 5, wherein said providing a phenyltetrahydrofuran compound of formula (IV) comprises providing a compound of formula (VI)

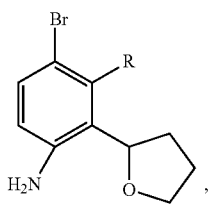

wherein R is H or F;
protecting the amino group of the compound of formula (VI) with an amino protecting group to afford an amino-protected compound;
nitrating the amino-protected compound with a suitable nitrating agent to afford an amino-protected nitro compound; and
deprotecting the amino-protected nitro compound to afford the phenyltetrahydrofuran compound of formula (IV).

10. The method of claim 1, wherein said providing a phenylpyrimidine compound of formula (II) further comprises reducing a phenylpyrimidine derivative of formula (V),

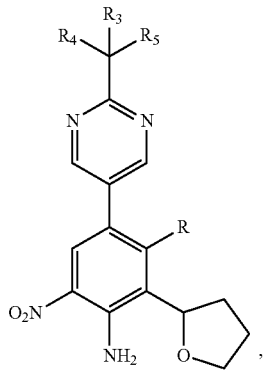

wherein R is H or F, and each of $R_3$, $R_4$, and $R_5$ is independently an optionally substituted alkyl or an optionally protected hydroxyl group,
with a suitable reducing agent to provide the compound of formula (II).

11. The method of claim 9, wherein said nitrating the compound of formula (VI) comprises reacting the compound of formula (VI) with $NH_4NO_3$ in the presence of a strong acid at about 20° C. to about 50° C. to provide a compound (IV).

12. The method of claim 9, wherein said providing a compound of formula (VI) comprises providing a compound of formula (VII),

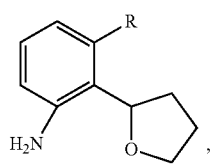

wherein R is H or F; and
reacting the compound of formula (VII) with a brominating agent in a polar aprotic solvent to afford the compound of formula (VI).

13. The method of claim 12, wherein the compound of formula (VII) is enantiomerically enriched.

14. The method of claim 12, wherein said providing a compound of formula (VII) comprises:
providing a dihydrofuranyl nitrobenzene compound selected from the group consisting of a compound of formula (VIIIa),

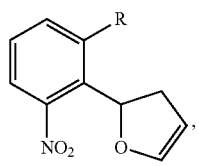

wherein R is H or F, and a compound of formula (VIIIb),

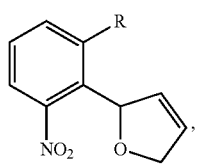

wherein R is H or F; and
treating the dihydrofuranyl nitrobenzene compound with a reducing agent to afford the compound of formula (VII).

15. The method of claim 14, wherein said providing a dihydrofuranyl nitrobenzene compound comprises:
providing a compound of formula (IX),

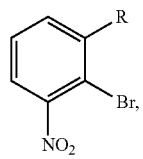

wherein R is H or F; and
treating the compound of formula (IX) with 2,3-dihydrofuran in the presence of a palladium catalyst to afford the dihydrofuranyl nitrobenzene compound.

16. A compound of formula (II)

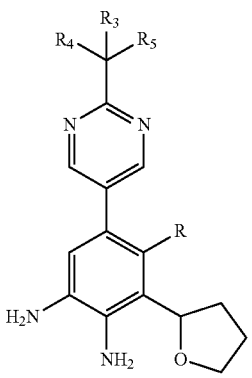

wherein
R is H or F, and each of R₃, R₄, and R₅ is independently an optionally substituted alkyl or an optionally protected hydroxyl group.

17. A compound of formula (V)

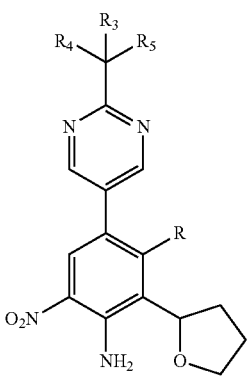

wherein R is H or F, and each of R₃, R₄, and R₅ is independently an optionally substituted alkyl or an optionally protected hydroxyl group.

18. A method for preparing a compound of formula (I)

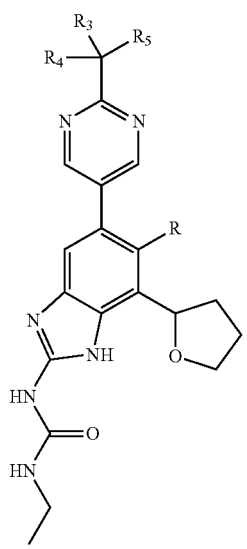

or a pharmaceutically acceptable salt thereof, wherein R is H or F; and each of R₃, R₄, and R₅ is independently an optionally substituted alkyl or an optionally protected hydroxyl group;
comprising providing a dihydrofuranyl nitrobenzene compound of formula (VIIIa),

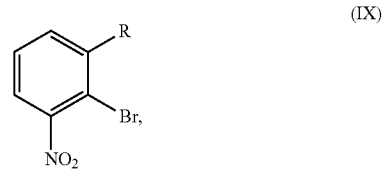

wherein R is H or F, and
converting the compound of formula (VIIIa) or (VIIIb), or a combination thereof, to the compound of formula (I) or a pharmaceutically acceptable salt thereof.

19. The method of claim 18, wherein said providing a dihydrofuranyl nitrobenzene compound of formula (VIIIa) or (VIIIb) comprises reacting a compound of formula (IX),

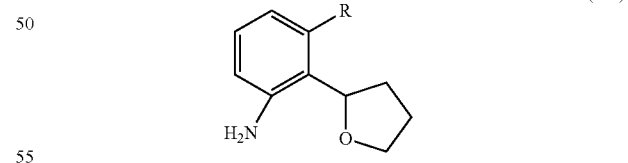

wherein R is H or F; with 2,3-dihydrofuran in the presence of a palladium catalyst to afford the dihydrofuranyl nitrobenzene compound (VIIIa) or (VIIIb).

20. The method of claim 19, further comprising reacting the compound of formula (VIIIa) or (VIIIb) with a reducing agent to afford a compound of formula (VII),

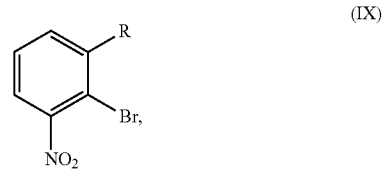

wherein R is H or F.

21. The method of claim 20, further comprising reacting the compound of formula (VII) with a brominating agent in a polar aprotic solvent to afford the compound of formula (VI).

22. The method of claim 21, further comprising nitrating the compound of formula (VI) with a suitable nitrating agent to afford the phenyltetrahydrofuran compound of formula (IV).

23. The method of claim 22, further comprising reacting the phenyltetrahydrofuran compound of formula (IV) with a boronic acid derivative of formula (III)

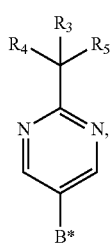

(III)

wherein each of $R_3$, $R_4$, and $R_5$ is independently an optionally substituted alkyl or an optionally protected hydroxyl group, and B* is

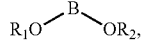

each of $R_1$ and $R_2$ being independently alkyl or H, or $OR_1$ and $OR_2$ together with the B atom to which they are attached forming an optionally substituted 5-, 6-, or 7-membered ring, or $BF_3X$, X being any monovalent cation, in the presence of a palladium catalyst in a polar solvent to provide a phenylpyrimidine compound of formula (V),

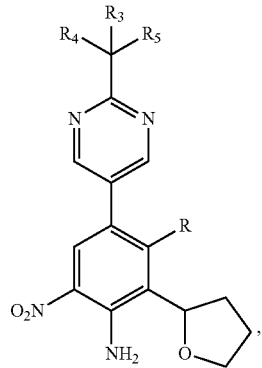

(V)

wherein R is H or F, and each of $R_3$, $R_4$, and $R_5$ is independently an optionally substituted alkyl or an optionally protected hydroxyl group; and treating the phenylpyrimidine compound of formula (V) with a suitable reducing agent to afford the phenylpyrimidine compound of formula (II).

24. The method of claim 23, further comprising reacting the phenylpyrimidine compound of formula (II) with a urea derivative of formula A or B:

A

B wherein $R_6$ is an optionally substituted alkyl, optionally substituted aryl, optionally substituted saturated or unsaturated carbocycle, or optionally substituted saturated or unsaturated heterocycle;

to provide a compound of formula (I); and optionally reacting the compound of formula (I) with a suitable acid to provide a pharmaceutically acceptable salt of the compound of formula (I).

* * * * *